(12) United States Patent
Liu et al.

(10) Patent No.: US 12,295,799 B2
(45) Date of Patent: May 13, 2025

(54) INTELLIGENT SURGICAL MARKER

(71) Applicant: New Jersey Institute of Technology, Newark, NJ (US)

(72) Inventors: Xuan Liu, Berkeley Heights, NJ (US); Yuwei Liu, Harrison, NJ (US)

(73) Assignee: New Jersey Institute of Technology, Newark, NJ (US)

( * ) Notice: Subject to any disclaimer, the term of this patent is extended or adjusted under 35 U.S.C. 154(b) by 348 days.

(21) Appl. No.: 17/847,911

(22) Filed: Jun. 23, 2022

(65) Prior Publication Data

US 2023/0200930 A1    Jun. 29, 2023

Related U.S. Application Data

(60) Provisional application No. 63/216,142, filed on Jun. 29, 2021.

(51) Int. Cl.
*A61B 90/00* (2016.01)
*A61B 5/00* (2006.01)
(Continued)

(52) U.S. Cl.
CPC ............ *A61B 90/39* (2016.02); *A61B 5/0066* (2013.01); *A61B 5/444* (2013.01); *G06T 1/0014* (2013.01);
(Continued)

(58) Field of Classification Search
CPC ....... A61B 90/39; A61B 5/0066; A61B 5/444; A61B 5/7267; A61B 2090/395;
(Continued)

(56) References Cited

U.S. PATENT DOCUMENTS

2017/0086675 A1 *  3/2017  Li ....................... A61B 5/0073
2019/0216574 A1 *  7/2019  Coleman ............... A61B 5/444
(Continued)

FOREIGN PATENT DOCUMENTS

CN           108510502 A  *  9/2018  ............ G06T 7/11

OTHER PUBLICATIONS

De Carvalho, N., et al. "Optical coherence tomography for margin definition of basal cell carcinoma before micrographic surgery—recommendations regarding the marking and scanning technique." Skin Research and Technology 24.1 (2018): 145-151. (Year: 2018).*

*Primary Examiner* — Sean D Mattson
(74) *Attorney, Agent, or Firm* — McCarter & English, LLP

(57) ABSTRACT

Surgical marker systems and methods for delineating a lesion margin of a subject are provided. An example system includes a handheld probe device configured to capture an optical coherence tomography (OCT) image and a processor coupled to a memory. The handheld probe device includes a handheld probe including a fiber-optic probe assembly and a marker assembly. The processor is configured to: segment, by a neural network, each pixels of the OCT into different tissue-type categories; generate one or more feature vectors based at least in part on the segmented pixels; determine, by a one-class classifier, a boundary location in the OCT image between a normal tissue and an abnormal tissue of the tissue structure; and control the marker assembly to selectively create a visible label on a tissue location of the subject, the tissue location corresponding to the boundary location.

20 Claims, 27 Drawing Sheets
(3 of 27 Drawing Sheet(s) Filed in Color)

(51) Int. Cl.
  *G06T 1/00* (2006.01)
  *G06T 7/00* (2017.01)
  *G06V 10/26* (2022.01)
  *G06V 10/774* (2022.01)
  *G06V 10/82* (2022.01)

(52) U.S. Cl.
  CPC ............ *G06T 7/0012* (2013.01); *G06V 10/26* (2022.01); *G06V 10/774* (2022.01); *G06V 10/82* (2022.01); *A61B 2090/395* (2016.02); *G06T 2207/10101* (2013.01); *G06T 2207/30088* (2013.01); *G06T 2207/30096* (2013.01); *G06T 2207/30204* (2013.01)

(58) Field of Classification Search
  CPC ...... A61B 2034/107; A61B 2090/3735; A61B 2090/3937; G06T 1/0014; G06T 7/0012; G06T 7/11; G06T 2207/10101; G06T 2207/30088; G06T 2207/30096; G06T 2207/30204; G06T 2207/20081; G06T 2207/20084; G06V 10/26; G06V 10/774; G06V 10/82; G06V 10/17; G06V 2201/032; G06V 2201/03; G16H 20/40; G16H 50/30; G16H 50/70; G16H 50/20; G16H 40/63; G16H 40/67; G16H 30/40
  See application file for complete search history.

(56) References Cited

U.S. PATENT DOCUMENTS

| | | | |
|---|---|---|---|
| 2021/0406596 A1* | 12/2021 | Hoffman | G06F 18/2163 |
| 2022/0108449 A1* | 4/2022 | Fan | G16H 50/30 |
| 2024/0087115 A1* | 3/2024 | Hong | G06V 10/82 |

* cited by examiner

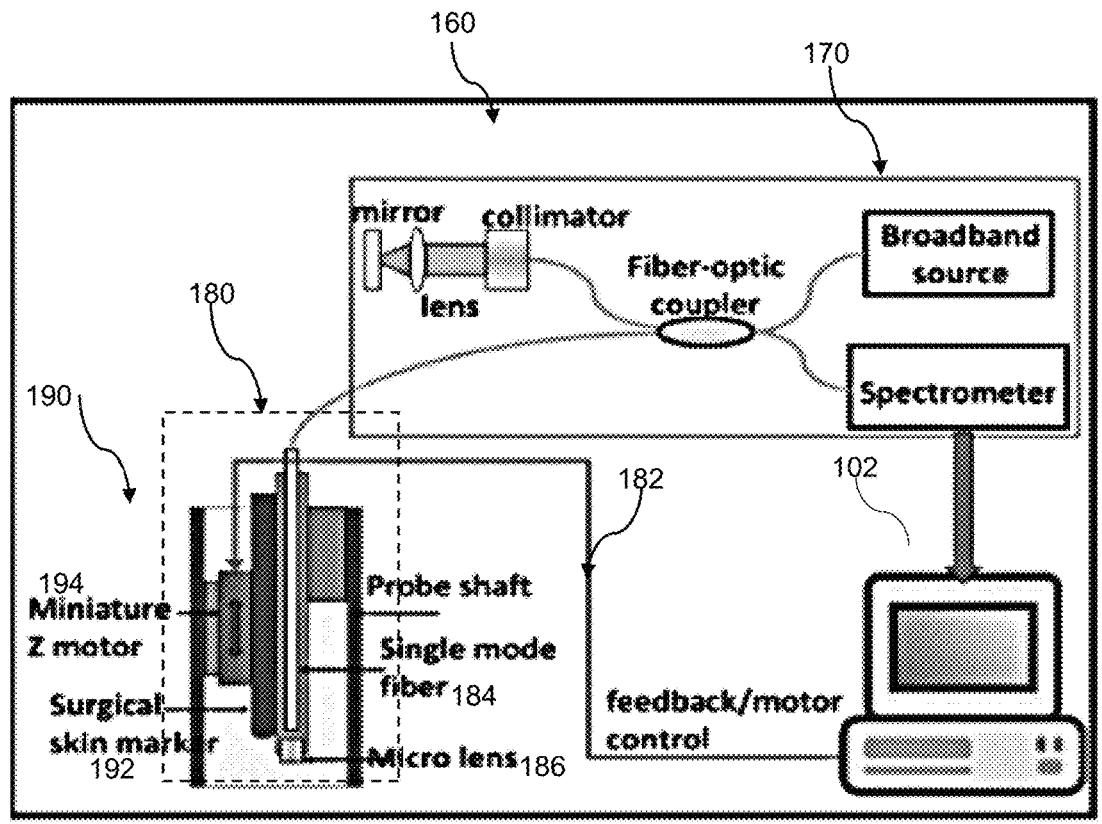
FIG. 2A
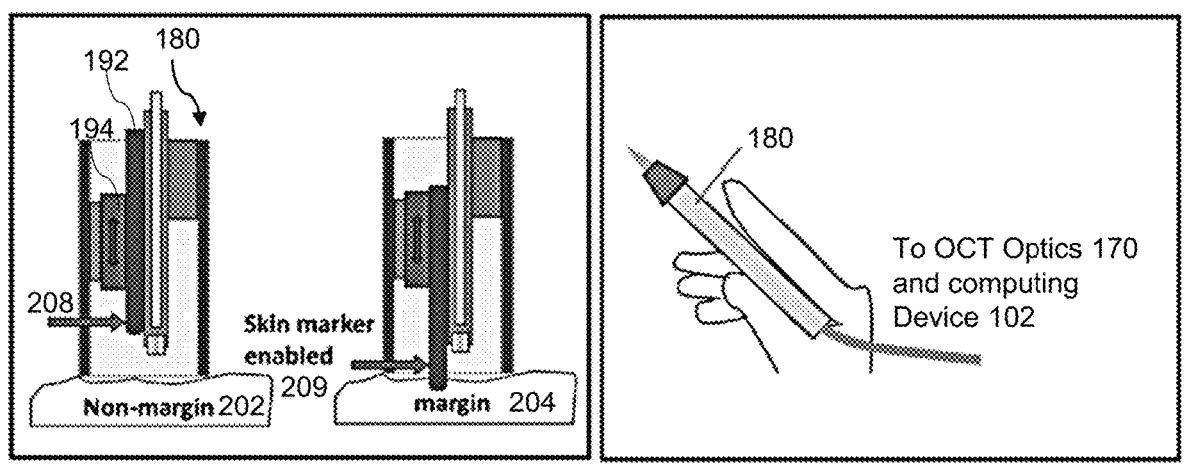
FIG. 2B
FIG. 2C

Scale bars represent 500μm.

Scale bars represent 500μm.

Scale bars represent 500μm.

Scale bars represent 500μm.

Scale bars represent 500μm.

Scale bars represent 500μm.

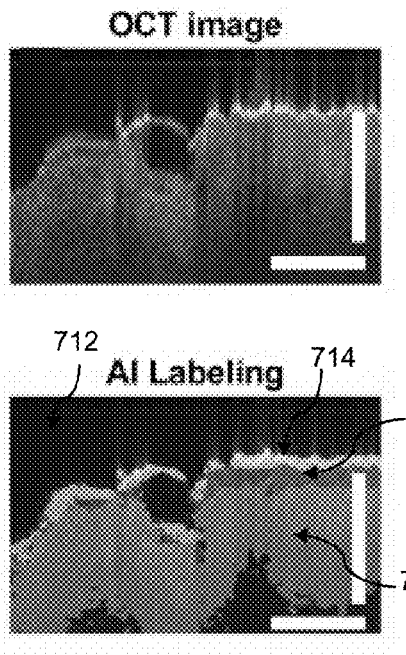
FIG. 8H
FIG. 8I
FIG. 8J
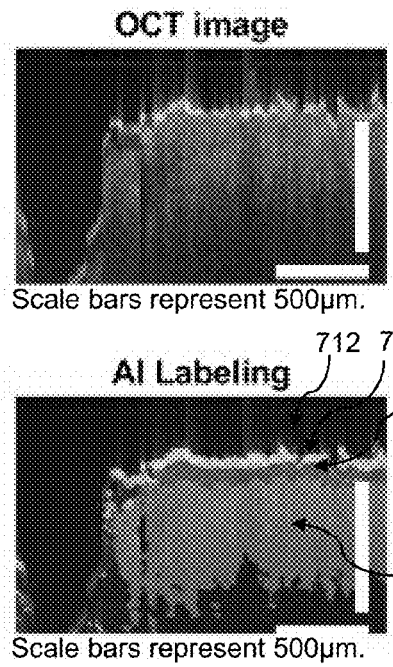
FIG. 8K
FIG. 8L
FIG. 8M
Scale bars represent 500μm.

OCT image

OCT image

Scale bars represent 500μm.

AI Labeling

AI Labeling

Scale bars represent 500μm.

OCT image

OCT image

Scale bars represent 500μm.

AI Labeling

AI Labeling

Scale bars represent 500μm.

E thickness

E thickness classification based on filtered prediction scores

INTELLIGENT SURGICAL MARKER

RELATED APPLICATIONS

This application claims priority to U.S. Provisional Application No. 63/216,142 filed on Jun. 29, 2021, the entire content of which is hereby incorporated by reference in its entirety.

BACKGROUND

Medical imaging techniques have been widely used to guide surgical procedures. Cross-sectional images taken before, during, and after surgery can provide information to develop a surgical plan, execute the surgical procedure, and evaluate the surgical outcome. However, medical imaging modalities, such as X-ray computed tomography (CT), magnetic resonance imaging (MRI), and ultrasound imaging, have macroscopic or mesoscale resolution, and do not have sufficiently high spatial resolution to reveal microscopic morphological features associated with skin pathology.

Nonmelanoma skin cancers (NMSCs) are the most common cancers in the United States. In 2012, the total number of NMSCs in the US was estimated to be more than 5.4 million and the number of patients receiving NMSC treatment was approximately 3.3 million. The number of newly diagnosed NMSC cases is projected to increase each year. Despite its prevalence, NMSCs have relatively small mortality if treated early.

Mohs micrographic surgery (MMS) is used widely to treat skin cancers. MMS provides the highest cure rates for NMSCs. From 1995 to 2009, the use of MMS increased by 400%, and currently 1 in 4 skin cancers is being treated with MMS. A major disadvantage of MMS is the long time needed to accomplish this surgical procedure. MMS on average takes one to two hours or longer, because the subsurface malignancy of NMSC often extends beyond the visible tumor margin identified in the initial clinical assessment. MMS is usually accomplished with multiple tissue excision stages, each followed by histological examination. Accordingly, there is a clinical need for image guidance of MMS and other types of surgeries.

SUMMARY

Described herein are systems and methods for delineating a lesion margin (e.g., skin lesion margin, a tumor margin, or the like) of a subject (e.g., a patient). In accordance with example embodiments of the disclosure, a surgical marker system is disclosed. The surgical marker system can be an optical coherence tomography (OCT) integrated surgical guidance platform. The surgical marker system can include a handheld probe device configured to capture one or more optical coherence tomography (OCT) images. The OCT image provides an in-depth cross sectional view of a tissue structure (e.g., a skin structure) beneath a tissue surface (e.g., a skin surface). The handheld probe device includes a handheld probe including a fiber-optic probe assembly and a marker assembly. The fiber-optic probe assembly is configured to direct low-coherence light to a region of interest and collect light reflected from the region of interest to acquire the OCT image(s). The marker assembly is configured to selectively create a visible label on the lesion margin of the subject. The surgical marker system can further include a processor coupled to a memory (e.g., a computer). The processor is configured to segment, by a neural network (e.g., U-Net neural network), each pixel of the OCT image into different tissue-type categories (e.g., a stratum corneum category, an epidermis category, and a dermis category); generate one or more feature vectors based at least in part on the segmented pixels; determine, by a one-class classifier (e.g., one-class support vector machine (SVM) classifier), a boundary location between a normal tissue and an abnormal tissue of the tissue structure based at least in part on the one or more feature vectors; and control the marker assembly to selectively create the visible label on a tissue location of the subject, the tissue location corresponding to the boundary location.

In accordance with other example embodiments of the disclosure, a method is disclosed for delineating a lesion margin of a subject. The method can include capturing one or more OCT images using low-coherence light. The OCT image provides an in-depth cross sectional view of a tissue structure beneath a tissue surface. The method can include segmenting, by a neural network, each pixel of the OCT image into different tissue-type categories. The method can include generating one or more feature vectors based at least in part on the segmented pixels. The method can determine, by a one-class classifier, a boundary location in the OCT image between a normal tissue and an abnormal tissue of the tissue structure based at least in part on the one or more feature vectors for each of the one or more OCT images. The method can further include controlling a marker assembly to selectively create the visible label on a tissue location of the subject, the tissue location corresponding to the boundary location.

Embodiments of the present disclosure can enable quantitative, objective, and data driven delineation of lesion margin and guide a surgeon to surgically remove lesions with higher accuracy compared to conventional systems and methods. The margin for tissue excision has been conventionally determined by the surgeon, following visual inspection that is qualitative, subjective, and largely dependent on the surgeon's training and experience. In contrast to the conventional systems and methods, the systems and methods of the present disclosure advantageously provide for contemporaneous and concurrent margin detection and marking that can achieve more accurate tissue excision (particularly at the first stage) and reduce the time required by using a single fiber OCT instrument that performs in vivo skin imaging and using machine learning for tumor boundary assessment and marking, leading to more accurate tumor margin detection.

It is not a trivial task to determine the condition of the skin by visually examining the OCT image. In clinical settings, an experienced reader who can interpret OCT data accurately is usually not available. Moreover, the results of visual inspection depend on the reader's training in dermatology and pathology, and can vary significantly. To extract clinically relevant information to guide the surgery, the challenge also comes from the fact that pathological features in OCT images are often obscured by speckle noise and depth dependent signal decay. To address the clinical need for accurate skin tissue characterization, the systems and methods taught herein provide a robust machine learning method that analyzes OCT images and performs automatic skin tissue classification, and further provide an approach to extract features learned by training a deep convolutional neural network (CNN) with a U-Net architecture, and to use the features to train the classifier to perform one-class SVM classification for anomaly detection. Compared to manually selected features in conventional methods, CNN features are extracted automatically at different abstract layers, and have the capability to provide a more objective and comprehensive characterization for the tissue.

It is also challenging to get a comprehensive training data set representing normal and abnormal skin tissue having various types, stages and grades of tumors. To overcome this challenge, the systems and methods taught herein train a one-class classifier to recognize normal skin tissue using OCT data obtained from healthy subjects. The classifier is able to detect the skin tumor as an anomaly regardless of cancer type, stage and grade.

Any combination and/or permutation of the embodiments is envisioned. Other objects and features will become apparent from the following detailed description considered in conjunction with the accompanying drawings. It is to be understood, however, that the drawings are designed as an illustration only and not as a definition of the limits of the present disclosure.

BRIEF DESCRIPTION OF THE DRAWINGS

The patent or application file contains at least one drawing executed in color. Copies of this patent or patent application publication with color drawing(s) will be provided by the Office upon request and payment of the necessary fee. To assist those of skill in the art in making and using the disclosed systems and methods, reference is made to the accompanying figures, wherein:

FIG. 2A illustrates an example embodiment of a surgical marker system in accordance with embodiments of the present disclosure.

FIG. 2B illustrates a handheld probe in FIG. 2A interacting with a tissue in accordance with embodiments of the present disclosure.

FIG. 2C illustrates an example exterior of the handheld probe in FIG. 2A in accordance with embodiments of the present disclosure.

FIG. 8H is an OCT image of the scar in FIG. 8A using a third scanning trajectory (6 o'clock direction) in FIG. 4A.

FIG. 8I is a U-Net segmentation image of the OCT image in FIG. 8H.

FIG. 8J illustrates an epidermal thickness along the lateral dimension of the OCT image in FIG. 8H.

FIG. 8K is an OCT image of the scar in FIG. 8A using a fourth scanning trajectory (9 o'clock direction) in FIG. 4A.

FIG. 8L is a U-Net segmentation image of the OCT image in FIG. 8K.

FIG. 8M illustrates an epidermal thickness along the lateral dimension of the OCT image in FIG. 8K.

DETAILED DESCRIPTION

Figure 1:
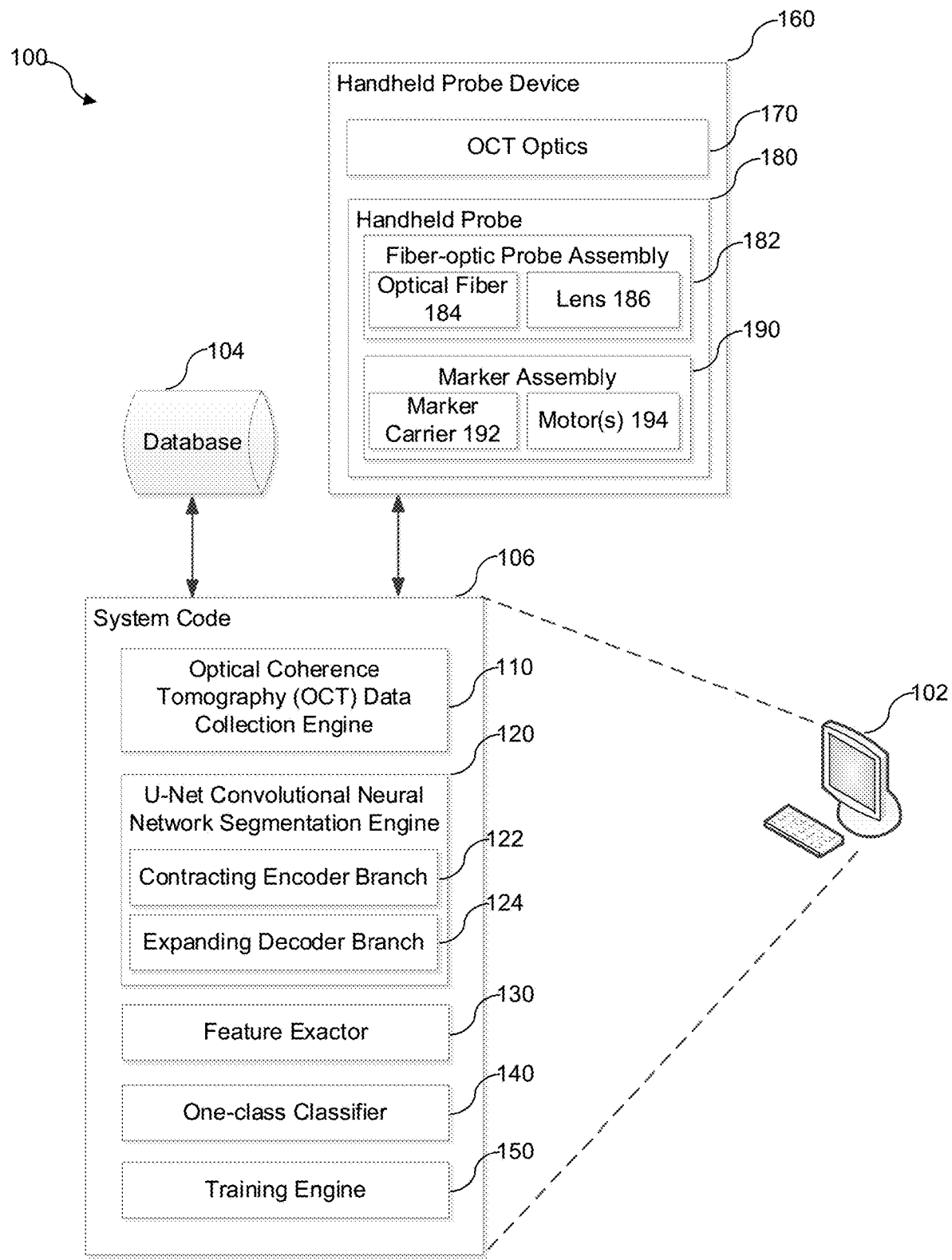
FIG. 1 is a diagram illustrating an example embodiment of a surgical marker system of the present disclosure.

The present disclosure relates to systems, methods, and computer-readable media for delineating (detecting and marking) a lesion margin of a subject. Example systems and methods are described in detail below in connection with FIGS. 1-19.

Optical coherence tomography (OCT) is a high resolution three dimensional (3D) imaging modality based on low coherence light interferometry. OCT has emerged as a valuable tool in many biomedical fields, including diagnostic ophthalmology, interventional cardiology, and surgical guidance. Compared to other medical imaging modalities, OCT allows subsurface skin imaging (~millimeter penetration depth) with microscopic spatial resolution and has great potential for surgical guidance. In addition, an OCT imaging probe can be miniaturized with fiber-optic components and can be conveniently integrated into a multifunctional, hand-held surgical instrument.

Successful application of OCT in surgical guidance remains challenging due to the following technical hurdles. First, a conventional OCT system has limited field of view (FOV) in both lateral and axial dimensions. Therefore, the area scanned by OCT is small and the sample must have a relatively flat surface topology to achieve an acceptable image quality. However, tumors can have significantly different lateral dimension and uneven surfaces. Therefore, a flexible scanning mechanism is needed to image different tumors for patients. Second, it is extremely challenging if not impossible to determine malignancy through visual examination of a massive OCT signal, because of the huge volume of data acquired (>1 gigabyte (GB) data per second), varying degree of information redundancy, and image features embedded in a variety of noise sources. Hence, there is a need to extract deep features from an OCT signal for automatic tissue classification and tumor margin delineation. Third, critical spatial locations (tumor margin) extracted through an OCT image analysis are defined in the coordinate system of the specific digital image. To precisely guide surgical excision of tissue, there is a need for a mechanism that registers spatial locations of interest back to the patient.

While an example embodiment of the present disclosure is described herein relative to Mohs micrographic surgery (MMS), exemplary embodiments can be implemented in other types of surgeries and procedures.

Embodiments of the present disclosure can provide systems and methods to delineate a lesion margin of a subject by integrating high-quality OCT imaging with (1) a lightweight probe that is manually and/or automatically scanned to perform OCT imaging on uneven surfaces with arbitrary lateral FOV; (2) artificial intelligence (AI) algorithms for automatic tissue classification and tumor margin detection; and (3) a mechanism that directly registers tumor margin back to the patient.

An example method for tumor margin detection in real time and/or real-time classification can include: (1) using experimental data (annotated images) to train a deep convolutional neural network (CNN) to segment different layers of the tissue, such as one with a U-Net architecture; (2) extracting features from the segmented image for different functional layers; (3) training a machine learning (ML) classifier to differentiate different tissues (normal versus pathological); (4) determining tumor margin as the location where the tissue transits from one type to another (normal to abnormal and vice versa) according to ML classification. To perform real-time classification margin detection, a computer software can load the pre-trained CNN and ML classifier into computer memory, can apply the CNN and ML classifier to data streaming into the computer in real-time, which provides tissue classification in real-time and identifies tumor margin as the location where the tissue transits from one type to another.

Turning to the drawings, FIG. 1 is a diagram illustrating an example embodiment of a surgical marker system 100 (also referred to as system 100 or intelligent surgical marker) of the present disclosure. The system 100 can be embodied as a computing device 102 (e.g., the computing device described with respect to FIG. 19) in communication with a database 104. The computing device 102 can include, but is not limited to, a computer system, a server, a personal computer, a cloud computing device, a smart phone, or any other suitable device programmed to carry out the processes disclosed herein. Still further, the system 100 can be embodied as a customized hardware component such as a field-programmable gate array ("FPGA"), an application-specific integrated circuit ("ASIC"), embedded system, or other customized hardware components without departing from the spirit or scope of the present disclosure. It should be understood that FIG. 1 is just one potential configuration, and that the system 100 of the present disclosure can be implemented using a number of different configurations.

The database 104 includes various types of data including, but not limited to, training OCT images, pre-trained/trained one-class classifier, pre-trained/trained neural network for segmentation (e.g., U-Net neural network), feature vectors, data associated with various components of the system 100 (e.g., an OCT data collection engine 110, a U-Net convolutional neural network segmentation engine 120, a contracting encoder branch 122, an expanding decoder branch 124, a feature extractor 130, a one-class classifier 140, a training engine 150, an OCT optics 170, a handheld probe 180, a fiber-optic probe assembly 182, an optical fiber 184, an optical lens 186, a marker assembly 190, a marker carrier 192, and a motor(s) 194, and/or other suitable components of the system 100).

The system 100 includes a handheld probe device 160 to capture OCT images of a lesion area of a subject. The handheld probe device 160 can include, but not limited to, the OCT optics 170 and the handheld probe 180. The OCT optics 170 can include various optical components (e.g., light source, low-coherence interferometry, mirror, collimator, lens, fiber-optic coupler, spectrometer, and other suitable optics for OCT imaging). The handheld probe 180 can include, but not limited to, the fiber-optic probe assembly 182 and the marker assembly 190. The fiber-optic probe assembly 182 is used to direct low-coherence light to a region of interest and collect light reflected from the region of interest. The fiber-optic probe assembly 182 can include, but not limited to, the optical fiber 184 and the optical lens 186. The marker assembly 190 is used to create a visible mark/label on the lesion margin of the subject. The marker assembly 190 can include, but not limited to, a marker carrier 192 configured to carry biomaterial to create a visible label on a tissue, and a motor(s) 194 configured to change a position of the marker carrier relative to the subject. Each component of the handheld probe device 160 is further described with respect to FIGS. 2A-2D.

The system 100 further includes system code 106 (non-transitory, computer-readable instructions) stored on a non-transitory computer-readable medium and executable by the hardware computing device 102 or one or more computer systems. The system code 106 can include various custom-written software modules that carry out the steps/processes described herein, and can include, but is not limited to, the OCT data collection engine 110, the U-Net convolutional neural network segmentation engine 120, the contracting encoder branch 122, the expanding decoder branch 124, the feature extractor 130, the one-class classifier 140, the training engine 150. Each component of the system code 106 is described with respect to FIGS. 5 and 10.

The system code 106 can be programmed using any suitable programming languages including, but not limited to, C, C++, C #, Java, Python, or any other suitable language. Additionally, the system code 106 can be distributed across multiple computer systems in communication with each other over a communications network, and/or stored and executed on a cloud computing platform and remotely accessed by a computer system in communication with the cloud platform. The system code 106 can communicate with the database 104, which can be stored on the same computer system as the system code 106, or on one or more other computer systems in communication with the system code 106.

Figure 2D:
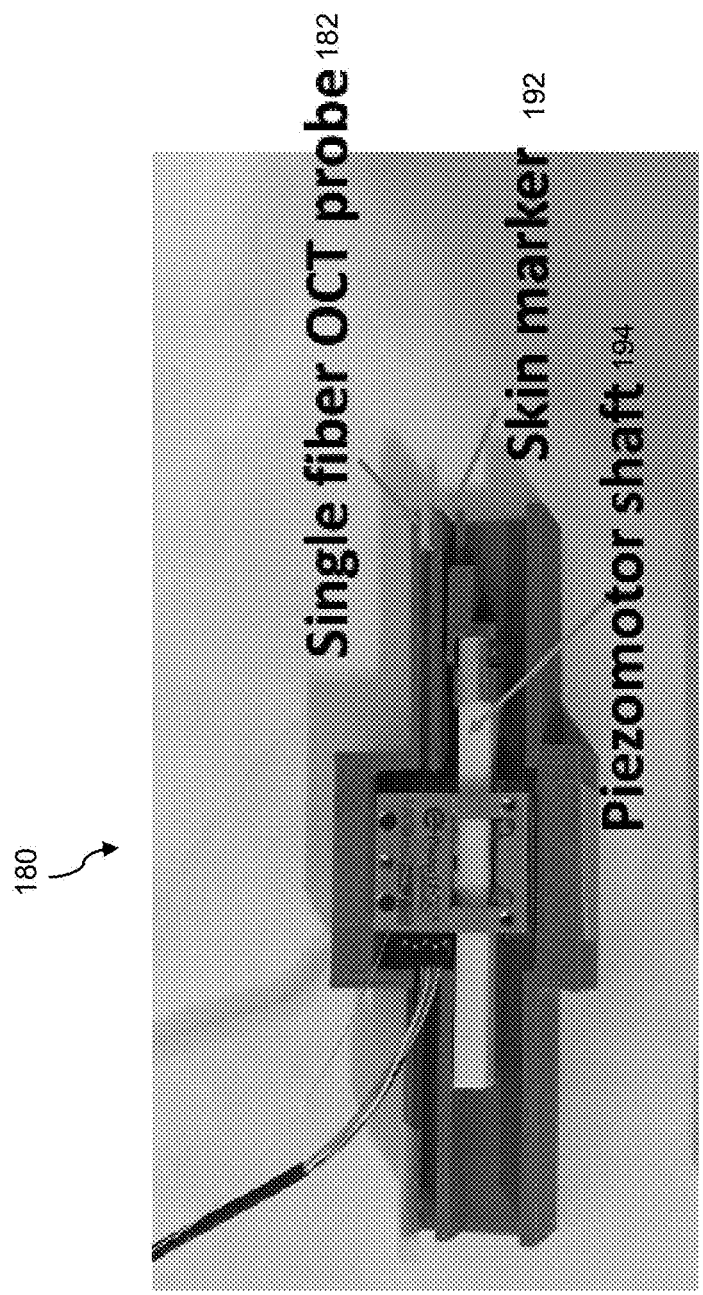
FIG. 2D is a schematic view of an example embodiment of the handheld probe in FIG. 2A.

FIG. 2A illustrates an example embodiment of the surgical marker system 100 in accordance with embodiments of the present disclosure. FIG. 2B illustrates the handheld probe 180 in FIG. 2A interacting with a tissue in accordance with embodiments of the present disclosure. FIG. 2C illustrates an example exterior of the handheld probe 180 in FIG. 2A in accordance with embodiments of the present disclosure. FIG. 2D is a schematic view of an example embodiment of the handheld probe 180 in FIG. 2A.

As shown in FIGS. 2A-2D, the system 100 can include the handheld probe device 160 having the OCT optics 170, the handheld probe 180 that interfaces with a subject (e.g., a patient), and the computing device 102 for signal/data analysis and device control. The OCT optics 170 can be an optical system to perform an OCT imaging. The OCT optics 170 can include a broadband source to emit light, a collimator to produce parallel light beams, a lens to focus the parallel light beams onto a mirror to form a reference arm, a single mode fiber 184 to direct light to a region of interest and a micro lens 186 to focus the light onto the region of interest to form a sample arm, and a spectrometer to collect light from the reference arm and the sample arm. A reflectivity profile, called an A-scan, provides in-depth cross sectional view of a tissue structure beneath a tissue surface and contains information about the spatial dimensions and location of structures. A cross-sectional tomogram (B-scan) can be achieved by laterally combining a series of these axial depth scans (A-scan).

The handheld probe 180 can include the single mode fiber 184 (in some embodiments, a multi-mode fiber can be used) to deliver light to a region of interest and light reflected from the region of interest to the spectrometer and the micro lens 186 to focus the light onto the region of interest and collect light reflected from the region of interest. The handheld probe 180 can further include the motor 194 (e.g., miniature z-motor) that actuates the marker carrier 192 carrying content (e.g., skin labeling biomaterial, or the like) up and down between a protracted position to reach a tumor margin for labeling and a retracted position to move the marker carrier back. The handheld probe 180 can further include a probe holder (e.g., a probe shaft). The handheld probe 180 can be in communication with the computing device 102 (e.g., a computer) and the OCT optics 170.

In some embodiments, the OCT optics 170 can be based on a Fourier domain OCT. The output of the broadband source (e.g., a light source providing low-coherence light) shown in FIG. 2A can be routed by a fiber optic circulator to the fiber-optic probe assembly 182. In some embodiments, the fiber-optic probe assembly 182 can be made by splicing a FC/APC single mode patch cable to a segment of bare fiber, integrating a distal tip of the optical fiber 184 with a needle and a rubber cap at its tip, and attaching the fiber-optic probe assembly 182 with a plastic handle. The metal needle shaft provides mechanical rigidity for the probe. The rubber cap ensures gentle contact between the probe and the skin, and minimizes the deformation of skin layers during scanning. The fiber tip can be cleaved to generate a flat surface. Through Fresnel reflection, the tip of the fiber-optic probe assembly 182 provides a reference light ($E_r$). The fiber-optic probe assembly 182 also collects signal photons from the sample ($E_s$). In the common path interferometer, $E_r$ and $E_s$ share the same probe path and interfere to extract depth resolved information from the sample. Unlike a conventional OCT imaging system based on a Michelson interferometer, the single fiber probe described herein enables common path OCT imaging where $E_r$ and $E_s$ share the same probe path. In addition, 2D images can be acquired through manual scanning. Speckle decorrelation analysis is performed to correct distortion artifacts. Although a single fiber probe is shown, it should be understood that a multi-fiber probe can be used.

The computing device 102 can receive data from the OCT optics 170 and the handheld probe 180 and process the received data. The computing device 102 can further control one or more components of the OCT optics 170 and the handheld probe 180 by sending instructions and/or feedback to the one or more components of the OCT optics 170 and the handheld probe 180.

The handheld probe 180 can acquire photons from a skin surface of a subject to interrogate a pathological status of skin tissue. The photons can be collected and analyzed by the OCT optics 170 that streams raw data into the computing device 102 for image reconstruction and analysis. Based on a deep convolutional neural network trained by experimental data, the computing device 102 can determine if the handheld probe 180 is acquiring signal from normal or abnormal tissue and can further determine a margin 204 of a tumor based on a transition between the normal tissue and the abnormal tissue. If non-margin 202 is detected, the computing device 102 can, concurrently with the detection of a non-margin 202, hold the marker carrier 192 in a retracted position 208 at a rest location within the handheld probe where the marker carrier 192 is away from a tissue surface. If the margin 204 is detected, the computing device 102 can control the motor 194, concurrently with detection of a margin, to move marker carrier 192 to a protracted position 209 protruding from the handheld probe onto the detected margin 204 to create a visible label on the margin 204. Examples for determining normal and abnormal tissues and lesion margins are described with respect to FIGS. 5, 8A-8M, 9A-9M, 14A-14F, 16A, 16B, and 16D-16K.

In some embodiments, the single mode fiber used for OCT imaging can be protected by a ceramic ferrule that also provides mechanical rigidity. The tip of the ferrule can be covered by a rubber cap that ensures gentle contact with the skin during image acquisition. The rubber cap also can create an axial offset between the fiber tip and the skin surface, which is critical in preventing sensor saturation and image artifacts. The handheld probe 180 also houses the miniature piezo motor 194 that actuates the skin marker 192 to perform data driven skin labeling. Once a margin between normal and abnormal tissue is identified using methods described herein, the miniature piezo motor 194 can be commanded to translate towards the surface of the skin to the protracted position 209, label the margin 204, and retract back into the probe to the retracted position 208.

Figure 3A:
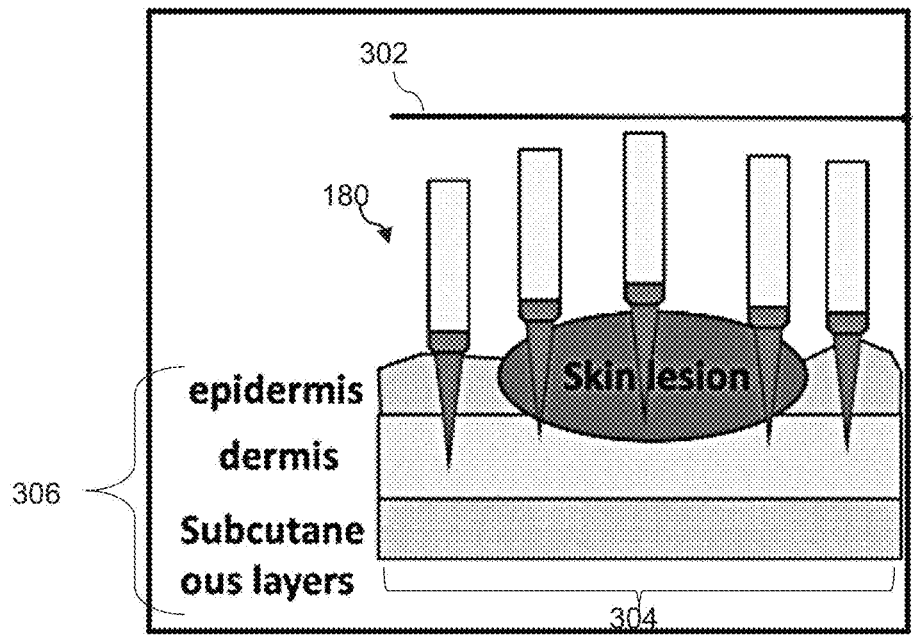
FIG. 3A illustrates the handheld probe in FIG. 2A scanning a lesion area in accordance with embodiments of the present disclosure.

FIG. 3A illustrates the handheld probe 180 in FIG. 2A scanning a lesion area in accordance with embodiments of the present disclosure. As shown in FIG. 3A, the handheld probe 180 can manually and/or automatically scan a region of interest 304 along a scanning direction 302. The region of interest 304 can include a skin lesion.

Figure 3B:
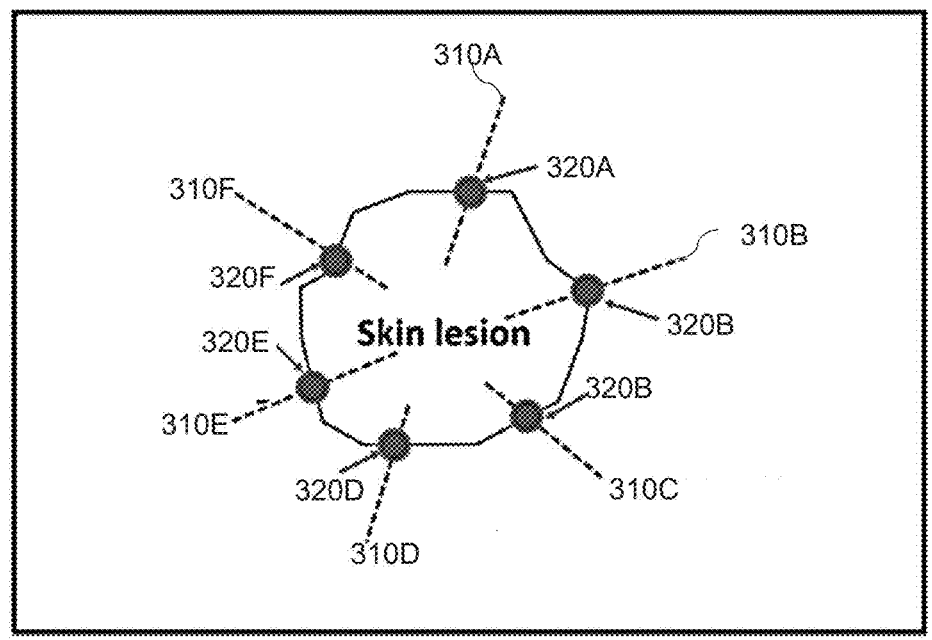
FIG. 3B illustrates a margin of a lesion labeled by the handheld probe in FIG. 2A via various scans in accordance with embodiments of the present disclosure.

FIG. 3B illustrates a margin of a lesion labeled by the handheld probe 180 in FIG. 2A via various scans in accordance with embodiments of the present disclosure. As shown FIG. 3B, the handheld probe 180 can perform multiple scans 310A-310F and find multiple margin locations 320A-320F. The handheld probe 180 can create a visible label at each margin location. A contour that precisely outlines the lateral extension of the tumor can be generated after a sufficient amount of manual and/or automatic scans is performed.

In some embodiments, if the computing device 102 determines the tissue under the handheld probe 180 is normal, the computing device 102 can control the marker assembly 190 to be inactive without creating any label at the tissue. If the computing device 102 determines the tissue under the handheld probe 180 is a boundary between normal tissue and diseased/abnormal tissue (tumor), the computing device 102 can activate the marker assembly 190 to create a visible label at the tissue, which can guide a surgical excision. The handheld probe 180 can manually and/or automatically scan an arbitrary lateral field of view and follow an uneven surface topology of a tissue (e.g., skin).

Unlike a conventional OCT imaging system, the system 100 can perform lateral scanning by manually and/or automatically steering the handheld probe 180 across a region of interest. Therefore, the imaging probe can be extremely simple, lightweight, and low cost. A motion tracking method can be utilized based on a speckle decorrelation analysis, to quantify the lateral displacement between adjacent Ascans and correct distortion artifact caused by manual scanning (e.g., when the probe is manually scanned, the resultant image has a nonconstant spatial sampling rate induced by the nonconstant scanning speed). Briefly, the cross-correlation $\rho_i$ is calculated between sequentially acquired Ascans ($S_i$ and $S_{i+1}$):

$$\rho_i = \frac{((S_i - \langle S_i \rangle)(S_{i+1} - \langle S_{i+1} \rangle))}{\sigma_i \sigma_{i+1}},$$

the cross-correlation coefficient is used to quantify lateral displacement:

$$\delta x_i = w_0 \sqrt{\ln\left(\frac{1}{\rho_i}\right)},$$

the accumulated lateral displacement is calculated $x_n = \Sigma_{i=1}^n \delta x_i$, and samples an Ascan when $x_n$ reaches $\Delta x$ that is the pre-determined lateral sampling interval. With the above motion tracking and Ascan resampling method, the present inventors are able to reconstruct distortion free OCT images using data obtained from manual scanning. The system 100 can acquire OCT signal using a frame grabber, processes signal in real-time using a graphics processing unit (GPU), and can use a Precision workstation to coordinate data acquisition, processing, and display.

Figure 4A:
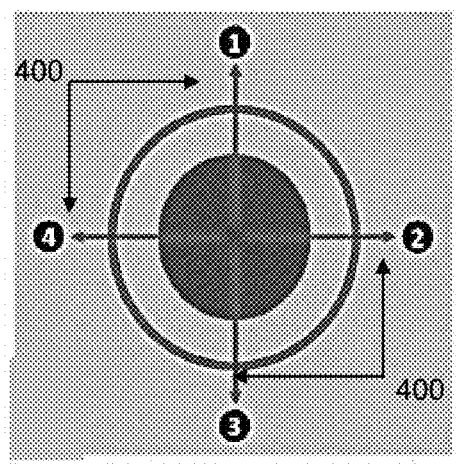
FIG. 4A schematically illustrates example scanning trajectories along a tumor, a surgical margin, and a normal skin.
Figure 4B:
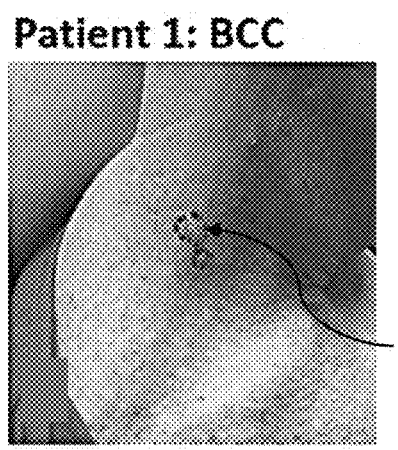
FIG. 4B is a clinical photograph of a basal cell carcinoma (BCC) tumor on a right neck imaged in a patient.
Figure 4L:
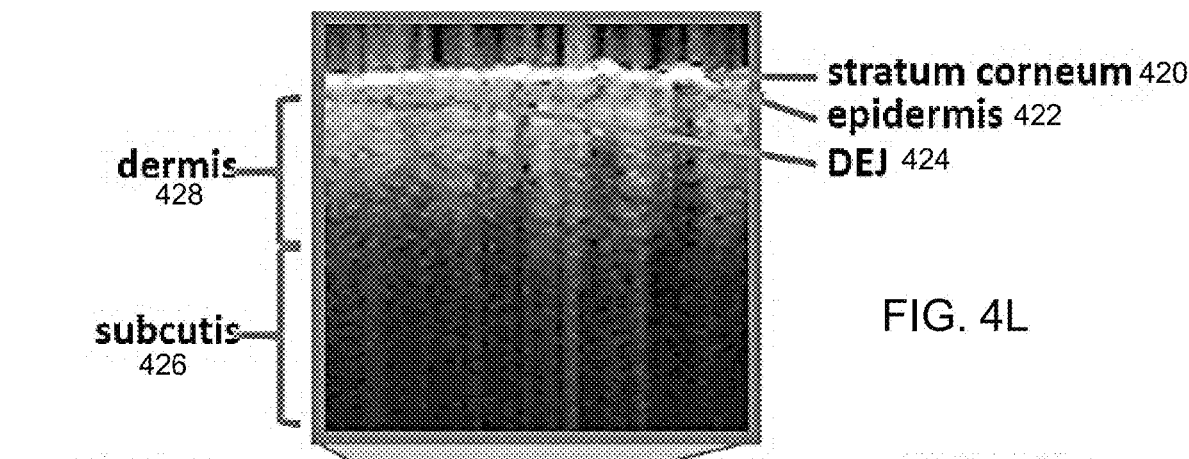
FIG. 4L is a magnified illustration of a normal tissue area in FIG. 4C.
Figures 4C, 4D:
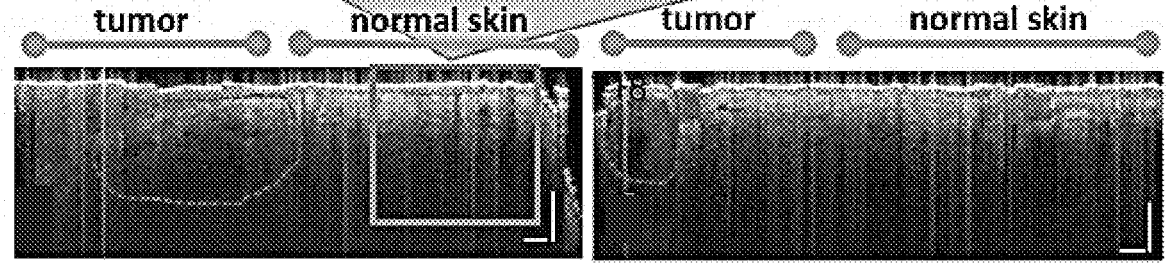
FIG. 4C is an OCT image of the BCC tumor in FIG. 4B using a first scanning trajectory (12 o'clock direction) in FIG. 4A.
FIG. 4D is an OCT image of the BCC tumor in FIG. 4B using a second scanning trajectory (3 o'clock direction) in FIG. 4A.
Figures 4E, 4F:
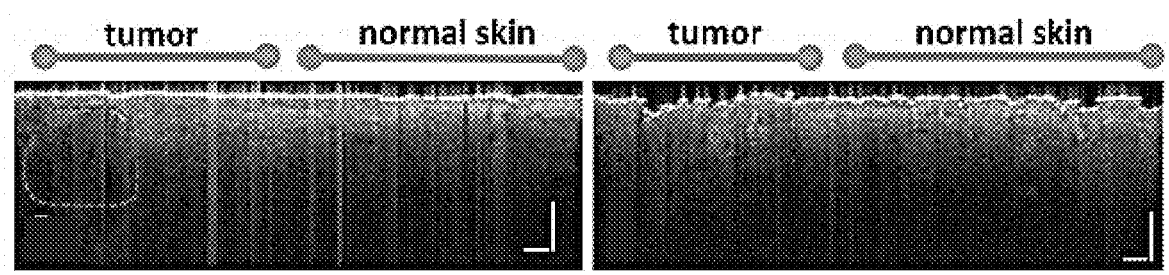
FIG. 4E is an OCT image of the BCC tumor in FIG. 4B using a third scanning trajectory (6 o'clock direction) in FIG. 4A.
FIG. 4F is an OCT image of the BCC tumor in FIG. 4B using a fourth scanning trajectory (9 o'clock direction) in FIG. 4A.
Figure 4G:
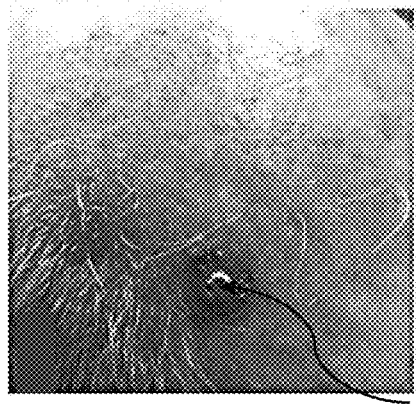
FIG. 4G is a clinical photograph of a squamous cell carcinoma (SCC) tumor on a scalp imaged in a patient.
Figures 4H, 4I:
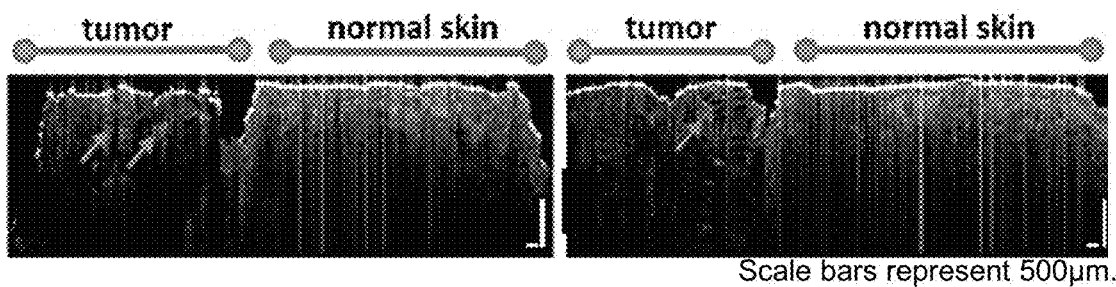
FIG. 4H is an OCT image of the SCC tumor in FIG. 4G using a first scanning trajectory (12 o'clock direction) in FIG. 4A.
FIG. 4I is an OCT image of the SCC tumor in FIG. 4G using a second scanning trajectory (3 o'clock direction) in FIG. 4A.
Figures 4J, 4K:
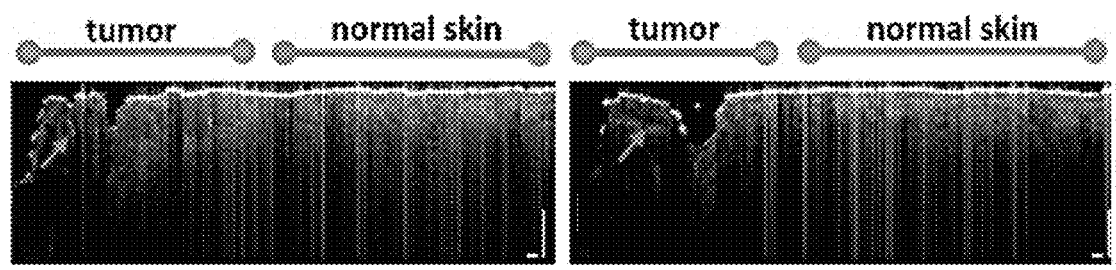
FIG. 4J is an OCT image of the SCC tumor in FIG. 4G using a third scanning trajectory (6 o'clock direction) in FIG. 4A.
FIG. 4K is an OCT image of the SCC tumor in FIG. 4G using a fourth scanning trajectory (9 o'clock direction) in FIG. 4A.

FIG. 4A schematically illustrates example scanning trajectories 400 along a tumor, a surgical margin, and a normal skin. FIG. 4B is a clinical photograph of a basal cell carcinoma (BCC) tumor 402 on a right neck imaged in a patient. FIG. 4C is an OCT image of the BCC tumor in FIG. 4B using a first scanning trajectory (12 o'clock direction) in FIG. 4A. FIG. 4D is an OCT image of the BCC tumor 402 in FIG. 4B using a second scanning trajectory (3 o'clock direction) in FIG. 4A. FIG. 4E is an OCT image of the BCC tumor 402 in FIG. 4B using a third scanning trajectory (6 o'clock direction) in FIG. 4A. FIG. 4F is an OCT image of the BCC tumor 402 in FIG. 4B using a fourth scanning trajectory (9 o'clock direction) in FIG. 4A. FIG. 4G is a clinical photograph of a squamous cell carcinoma (SCC) tumor 403 on a scalp imaged in a Patient. FIG. 4H is an OCT image of the SCC tumor 403 in FIG. 4G using a first scanning trajectory (12 o'clock direction) in FIG. 4A. FIG. 4I is an OCT image of the SCC tumor 403 in FIG. 4G using a second scanning trajectory (3 o'clock direction) in FIG. 4A. FIG. 4J is an OCT image of the SCC tumor 403 in FIG. 4G using a third scanning trajectory (6 o'clock direction) in FIG. 4A. FIG. 4K is an OCT image of the SCC tumor 403 in FIG. 4G using a fourth scanning trajectory 4 (9 o'clock direction) in FIG. 4A. FIG. 4L is a magnified illustration of a normal tissue area in FIG. 4C. The scan trajectories described with references to FIGS. 4A-4L are example trajectories and the numbering associated with the trajectory is no meant to impart an order with which the trajectories are performed, but rather to distinguish one trajectory from a another. Additional or different trajectories can be used to detect and mark a margin between norm and abnormal skin.

To demonstrate different signal characteristics for tumor and normal skin in the same OCT image, FIGS. 4C-4K present results obtained from two patients (Patient 1 with BCC and Patient 2 with SCC). Two-dimensional (2D) OCT images were obtained by manually scanning the single fiber probe (e.g., the handheld probe 180) across the skin tumors, along trajectories indicated by arrows in FIG. 4A. Ascans were sampled with a large lateral interval (e.g., about 51 micrometers) to achieve a sufficiently large FOV and cover a center of a tumor, a tumor margin, and adjacent normal skin tissues. Each OCT scanning started from the center of the tumor, moved beyond the margin labeled by the surgeon, and ended at normal skin tissues. Hence, the left part of each OCT scan corresponds to the tumor indicated by bars on the left above the OCT images in FIGS. 4C-4K. When the probe (e.g., the handheld probe 180) moved to normal tissue surrounding the tumor (e.g., right part of each OCT image, indicated by normal-skin bars above the OCT images in FIGS. 4C-4K), OCT signals showed a uniform epidermis, with a clear transition representing the dermo-epidermal junction (DEJ) 424. This can be seen more clearly in a magnified illustration in FIG. 4L that shows a bright stratum corneum 420, homogenous medium grey epidermis 422, a darker grey DEJ 424 representing a clear transition to the underlying light grey dermis 428, and dark grey-black subcutis 426. In each OCT image, regions corresponding to the tumor (e.g., the BCC tumor 402 or the SCC tumor 403) show a disrupted epidermis, losing the clear demarcation between the dermis and epidermis. Moreover, manual scanning images (FIGS. 4C-4F) obtained from BCC tumor 402 also show BCC features, including plug-like structures and upper dermis signal-free cavities (areas enclosed by dashed lines). Manual scanning images (FIGS. 4H-4K) obtained from SCC tumor 403 show SCC features, including a highly reflective surface with discrete bright regions below the surface (indicated by arrows).

Figure 5:
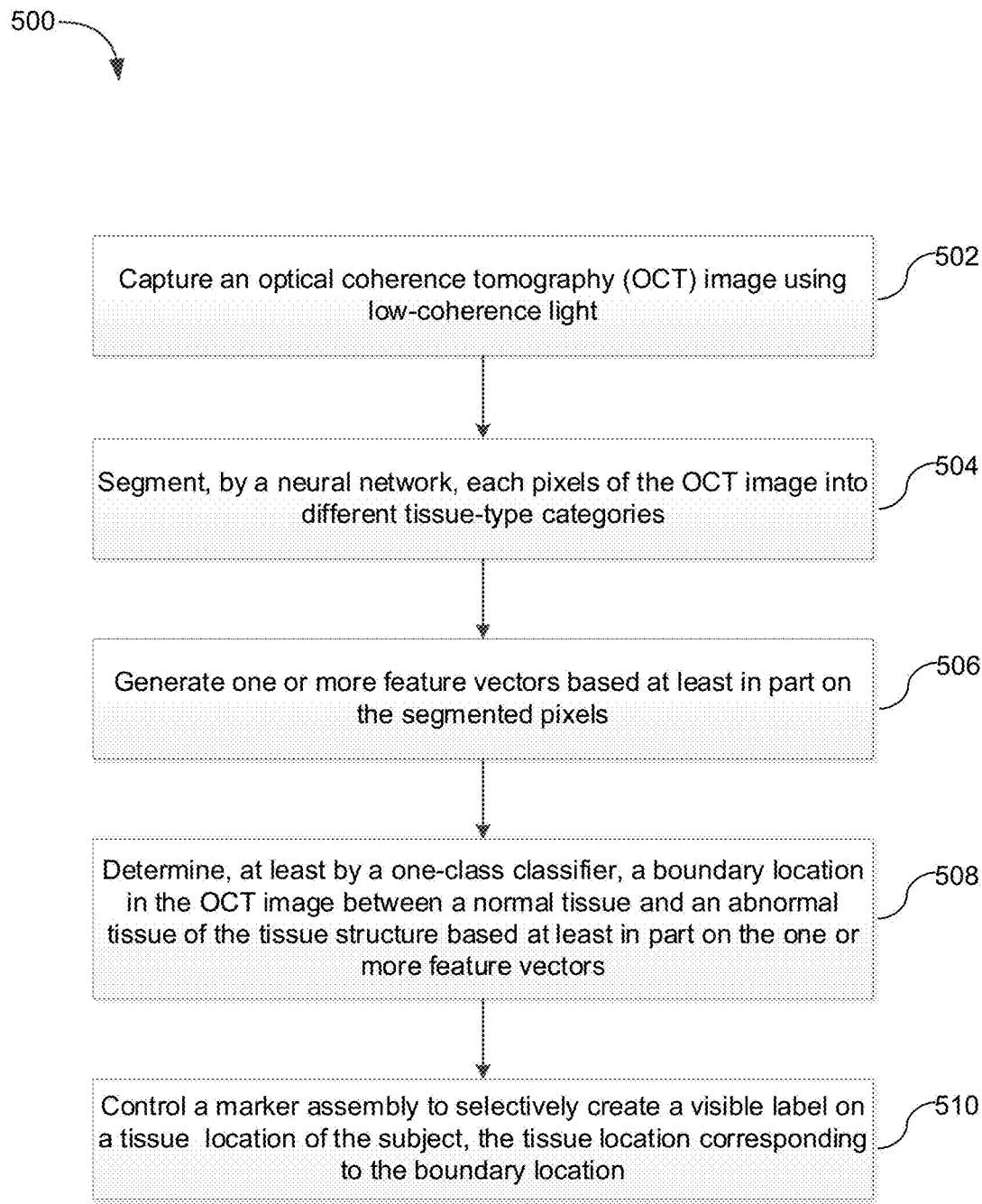
FIG. 5 is a flowchart illustrating overall processing steps carried out by the system of the present disclosure.

FIG. 5 is a flowchart illustrating overall processing steps 500 carried out by the system 100 of the present disclosure. In step 502, the system 100 captures one or more OCT images using low-coherence light. For example, as shown in FIGS. 1, 2A-2D, 3A and 3B, the OCT collection engine 110 can control the OCT optics 170 and/or the handheld probe 180 to capture one or more OCT images. Examples of OCT images are described with respect to FIGS. 4A-4K, 7-9, 14, and 16.

In step 504, the system 100 segments, by a neural network, each pixels of the OCT image into different tissue-type categories. For example, the U-Net convolutional neural network segmentation engine 110 can segment each pixel of the OCT image into different tissue-type categories. For example, as shown in FIG. 3A, a skin tissue 306 can have a stratum corneum category, an epidermis category, and a dermis category. Example segmentations using the U-Net convolutional neural network is further described with respect to FIGS. 6, 7A-7C, 8A-8M, and 9A-9M.

In step 506, the system 100 generates one or more feature vectors based at least in part on the segmented pixels. In some embodiments, the feature extractor 130 can generate feature vectors using activated and segmented OCT images. For example, the system 100 (e.g., the U-Net CNN segmentation engine 120) forward propagates the OCT image through the trained U-Net neural network up to a layer (e.g., an abstraction layer) prior to a segmentation layer of the U-Net neural network. The system 100 can determine an activation value as a result of forward propagation for each pixel of the OCT image corresponding to each filter. The activation values can be used to generate the feature vectors as further described with respect to FIGS. 11 and 12B. In some embodiments, the system 100 can determine a spatial variation in thickness of a segmented tissue structure (e.g., epidermis, dermis) associated with a particular tissue-type category based at least in part on the segmented pixels and the spatial variation in thickness of the segmented tissue structure can be sued to generate a feature vector as further described with respect to FIGS. 8D, 8G, 8J, 8M, 9D, 9G, 9J, 9M, and 13.

In step 508, the system 100 determines, by a one-class classifier, a boundary location in the OCT image between a normal tissue and an abnormal tissue of the tissue structure based at least in part on the one or more feature vectors. For example, the system 100 can determine a lesion margin based on prediction scores. The one-class classifier 140 (e.g., one-class support vector machine (SVM) classifier) can generate a prediction score for each pixel of each of the one or more OCT images. A prediction score indicative of the normal tissue is greater than a threshold value, and a prediction score indicative of the abnormal tissue is less than the threshold value. A threshold value refers to a value or a range indicative of a normal tissue. In some embodiments, a threshold value can be zero. A positive score is indicative of a normal tissue, and a negative score is indicative of an abnormal tissue. The system 100 can determine a pixel location as the boundary location. The pixel location of the boundary location corresponds to where a transition occurs between the prediction score indicative of the normal tissue and the prediction score indicative of the abnormal tissue.

Examples of determining lesion margins using prediction scores are described with respect to FIGS. 14A-14F.

In step 510, the system 100 controls a marker assembly to selectively create a visible label on a tissue location of the subject. The tissue location corresponds to the boundary location. For example, as shown in FIGS. 1, 2A and 2B, the marker assembly 190 includes the marker carrier 192 and the motor 194. The processor can control the motor 194 to place, from a rest location 208 of the marker carrier 192, the marker carrier 192 proximate to the tissue location 206 or one of 320A-320F based at least in part on the determination of the boundary location such that the marker carrier 192 is activated to create the visible label on the tissue location 206 or one of 320A-320F. Subsequent to creation of the visible label on the tissue location, the computing device 102 can control the motor 194 to move the marker carrier 192 back to the rest location 208. If the system 100 determines that a tissue under the handheld probe 180 is a normal tissue, the computing device 102 can control the motor 194 to hold the marker carrier 192 at the rest location 208.

The system 100 can covert the boundary location from an image-based coordinate system (e.g., coordinate system used for OCT images) to a subject-based coordinate system (e.g., real world coordinate system or a coordinate system used for tissues and/or subjects). For example, the system 100 can perform an image registration to transform pixel locations on the OCT images to corresponding tissue locations on the subject (e.g., patient) such that the system 100 can label the lesion margin on the subject and a surgeon can extract the lesion from the subject based on the labeled lesion margin.

Figure 6:
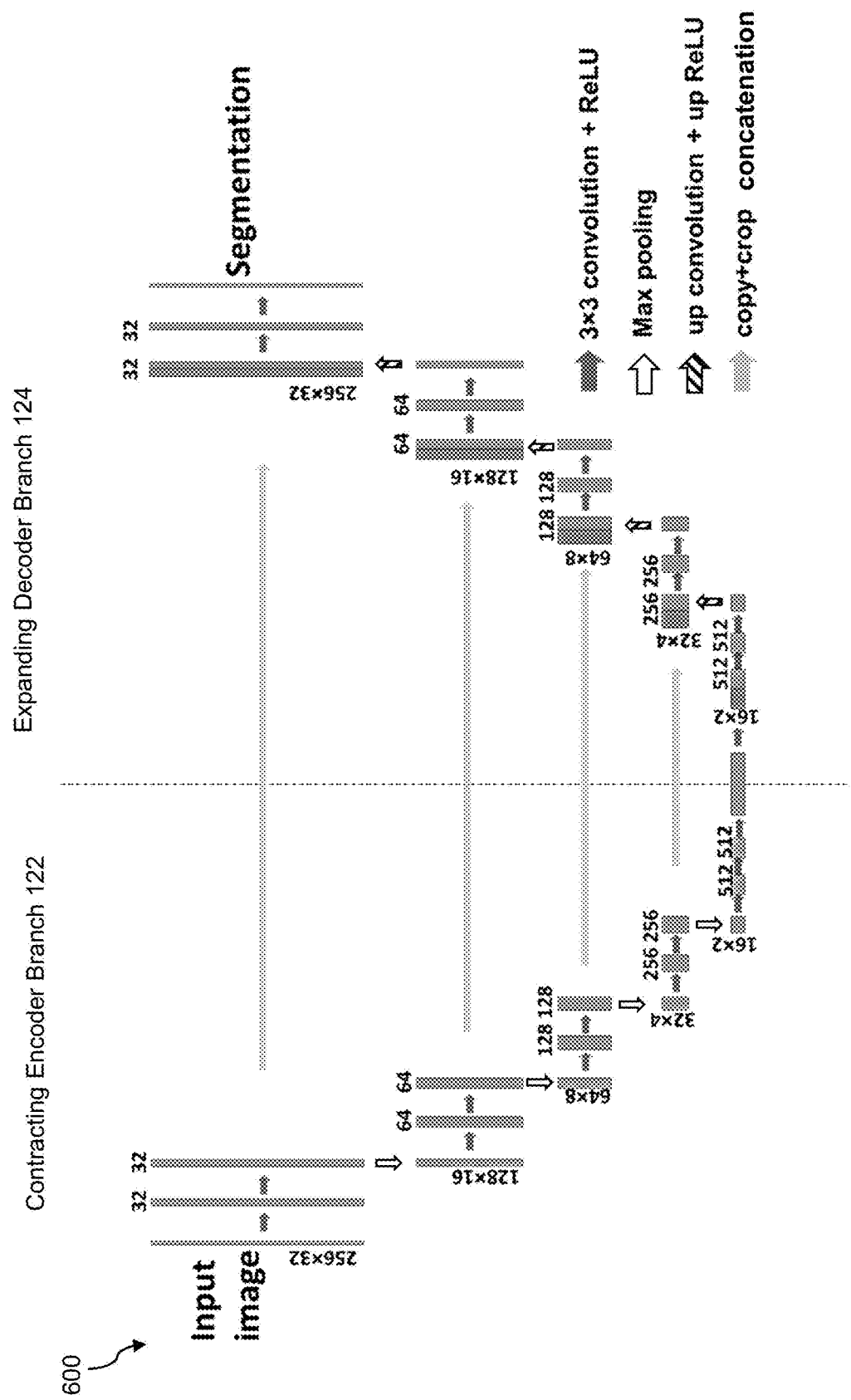
FIG. 6 illustrates a U-Net architecture for dermal OCT image segmentation.

FIG. 6 illustrates a U-Net architecture 600 for dermal OCT image segmentation. The U-Net architecture 600 allows quantitative assessment of epidermal thickness, automatically, and with high accuracy, for normal skin and skin lesions. As shown in FIG. 6, the U-Net architecture 600 has the contracting encoder branch 122 and the expanding decoder branch 124. The contracting encoder branch 122 has five stages to extract multiscale features of an input image (e.g., an OCT image captured by the handheld probe device 160) while the expanding decoder branch 124 has five stages to generate a spatially resolved prediction of individual pixels for segmentation. Each encoder stage has five layers including a 3×3 convolution layer, a rectified linear activation function (ReLU) activation layer, a 3×3 convolution layer, an ReLU activation layer, and a max pooling layer). Each decoder stage has seven layers including an up convolution layer for upsampling, an up ReLU layer, a concatenation layer, a 3×3 convolution layer, a ReLU layer, a 3×3 convolution layer, and a ReLU layer. The U-Net architecture 600 has input and output images with a dimension of 256 (axial dimension or z dimension)×32 (lateral dimension or x dimension) for illustration. In lateral dimension, the image input into the U-Net architecture 600 has 32 Ascans. It should be understood that the contracting encoder branch 122 and the expanding decoder branch 124 can have different number of stages and each stage can have different number of layers, and the input and output images can have different dimensions.

The system 100 (e.g., U-Net convolutional neural network segmentation engine 120) can use a neural network with the U-Net architecture 600 to perform tasks including DEJ assessment (examples are described with respect to FIGS. 7A-7C, 8A-8M, and 9A-9M) and skin layer thickness quantification (examples are described with respect to FIGS. 8A-8M, and 9A-9M).

Figure 7A:
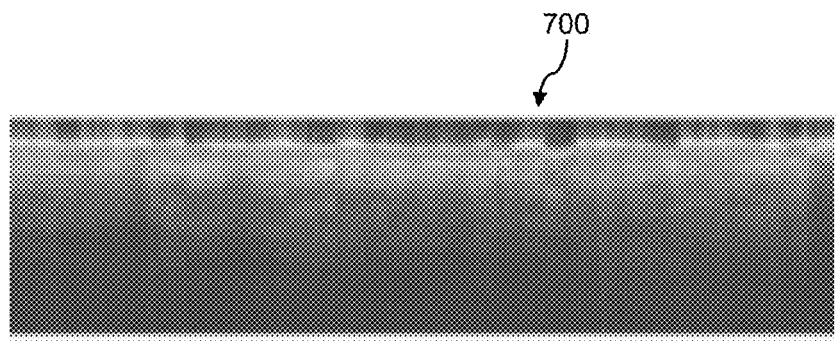
FIG. 7A is an OCT image of a skin tissue.
Figure 7B:
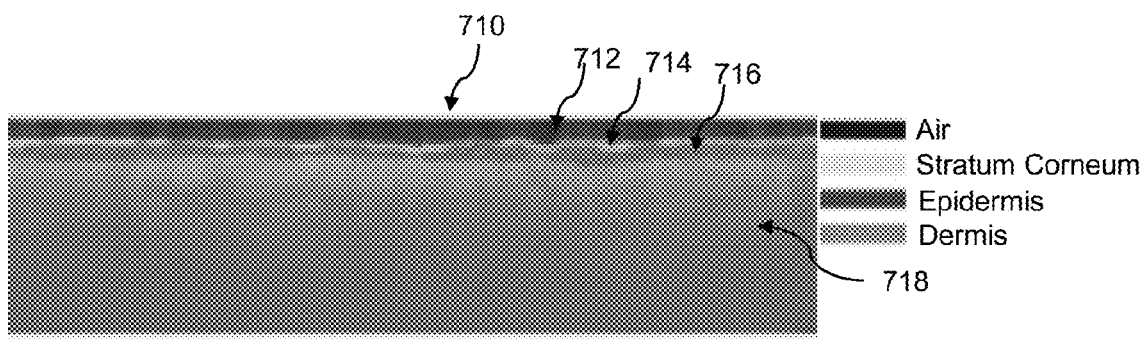
FIG. 7B is a ground truth image providing ground truth labels for the OCT image in FIG. 7A.
Figure 7C:
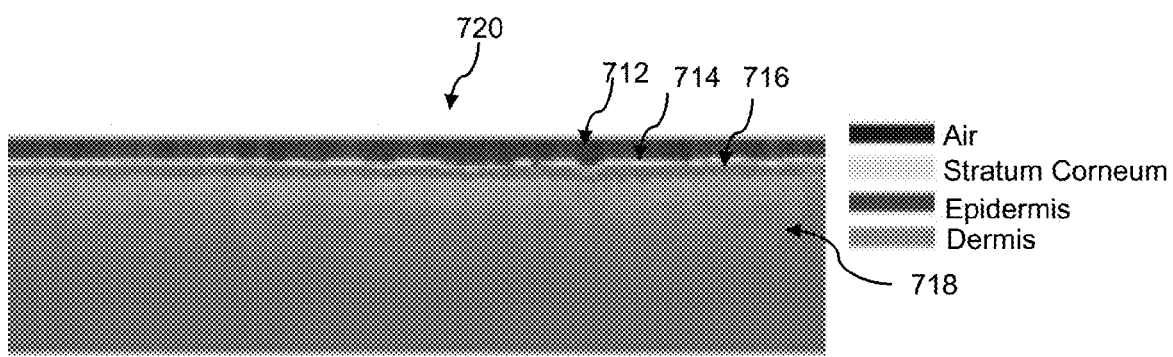
FIG. 7C is a segmented OCT image having labels generated by the U-Net architecture in FIG. 6 for individual pixels of the OCT image in FIG. 7A.

FIG. 7A is an OCT image 700 of a skin tissue. FIG. 7B is a ground truth image 710 providing ground truth labels for the OCT image 710 in FIG. 7A. FIG. 7C is a segmented OCT image 720 having labels generated by the U-Net architecture 600 for individual pixels of the OCT image 700 in FIG. 7A.

As shown in FIGS. 7A-7C, the neural network with the U-Net architecture 600 can perform DEJ assessment (also referred to as the DEJ segmentation) by generating rules to assign a label (e.g., air 712, stratum corneum 714, epidermis 716, or dermis 718) to every pixel of the OCT image 700. The neural network with the U-Net architecture 600 can be trained using image data (e.g., the OCT image 700) and ground truth pixel classification (e.g., the ground truth image 710 based on manual annotation data) to segment the OCT image 700 into layers including air 712, stratum corneum 714, epidermis 716, and dermis 718 (e.g., the segmented OCT image 720). In some embodiments, cross entropy can be used as the loss function for the U-net neural network. For each pixel, the neural network with the U-Net architecture 600 can effectively calculate a likelihood indicative of a pixel belonging to a specific category (e.g., air 712, stratum corneum 714, epidermis 716, and dermis 718). That pixel can be assigned a category that corresponds to the highest probability.

Figure 8A:
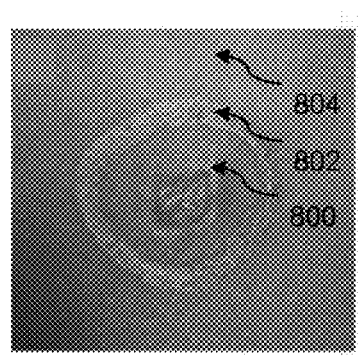
FIG. 8A is a photograph of a scar induced by laser irradiation.
Figure 8B:
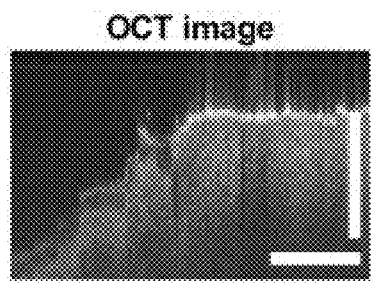
FIG. 8B is an OCT image of the scar in FIG. 8A using a first scanning trajectory (12 o'clock direction) in FIG. 4A.
Figure 8E:
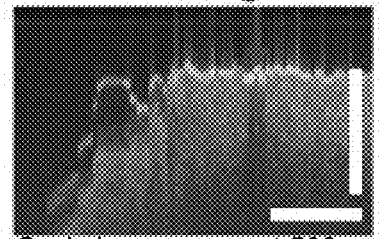
FIG. 8E is an OCT image of the scar in FIG. 8A using a second scanning trajectory (3 o'clock direction) in FIG. 4A.
Figure 8C:
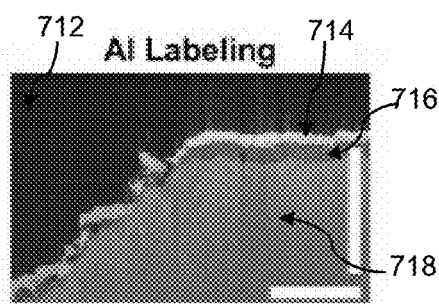
FIG. 8C is a U-Net segmentation image of the OCT image in FIG. 8B.
Figure 8F:
FIG. 8F is a U-Net segmentation image of the OCT image in FIG. 8E.
Figure 8D:
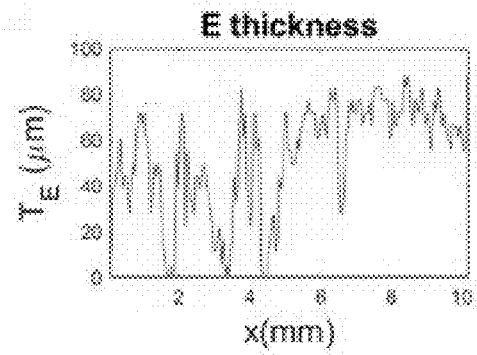
FIG. 8D illustrates an epidermal thickness along the lateral dimension of the OCT image in FIG. 8B.
Figure 8G:
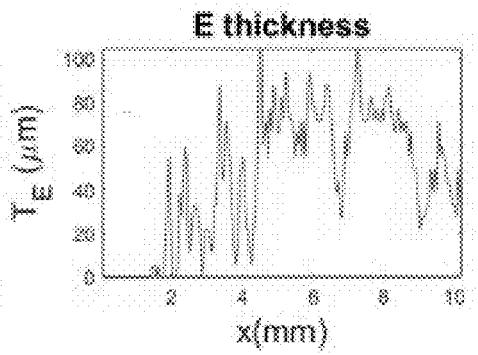
FIG. 8G illustrates an epidermal thickness along the lateral dimension of the OCT image in FIG. 8E.

FIG. 8A is a photograph of a scar 800 induced by laser irradiation. FIG. 8B is an OCT image of the scar 800 in FIG. 8A using a first scanning trajectory (12 o'clock direction) in FIG. 4A. FIG. 8C is a U-Net segmentation image of the OCT image in FIG. 8B. FIG. 8D illustrates an epidermal thickness along the lateral dimension of the OCT image in FIG. 8B. FIG. 8E is an OCT image of the scar 800 in FIG. 8A using a second scanning trajectory (3 o'clock direction) in FIG. 4A. FIG. 8F is a U-Net segmentation image of the OCT image in FIG. 8E. FIG. 8G illustrates an epidermal thickness along the lateral dimension of the OCT image in FIG. 8E. FIG. 8H is an OCT image of the scar 800 in FIG. 8A using a third scanning trajectory (6 o'clock direction) in FIG. 4A. FIG. 8I is a U-Net segmentation image of the OCT image in FIG. 8H. FIG. 8J illustrates an epidermal thickness along the lateral dimension of the OCT image in FIG. 8H. FIG. 8K is an OCT image of the scar 800 in FIG. 8A using a fourth scanning trajectory (9 o'clock direction) in FIG. 4A. FIG. 8L is a U-Net segmentation image of the OCT image in FIG. 8K. FIG. 8M illustrates an epidermal thickness along the lateral dimension of the OCT image in FIG. 8K.

In FIG. 8A, the scar 800 was located at a forearm of a subject. The scar 800 was formed by irradiating the skin with carbon dioxide ($CO_2$) fractional laser (5 millijoules (mJ), density 40% laser pulses) seven days prior to the imaging experiments. The age of the scars evaluated corresponds to the proliferative stage of wound healing—correlating to the timeline when a patient would typically return for MMS of a lesion that had recently been biopsied.

In FIG. 8B, the right side of the OCT image shows normal skin. The arrow indicates a mark 802 in FIG. 8A of a metallic ink pen. In comparison, the scar tissue 800 on the left side of the OCT image shows a thin and bright surface layer, followed by a signal void layer with significantly reduced OCT magnitude and then a layer with increased signal magnitude.

In FIG. 8C, for normal skin 804, the layer identified as epidermis by U-Net has a slowly varying thickness along the lateral dimension. As to the scar tissue 800, a layer identified as epidermis 716 using the U-Net architecture 600 has significantly different thickness along the lateral dimension.

In FIG. 8D, the thickness of the epidermis fluctuates drastically within the lesion and diminishes to zero at some locations, suggesting an altered skin structure associated with scarring. Results obtained from other scanning trajectories in FIGS. 8E-8M show similar contrast between the normal skin 804 and the scar 800.

Figure 9A:
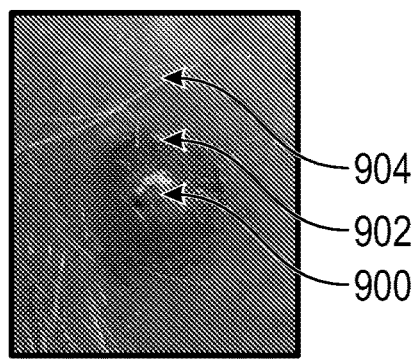
FIG. 9A is a photograph of a SCC tumor at a forehead of a patient.
Figure 9B:
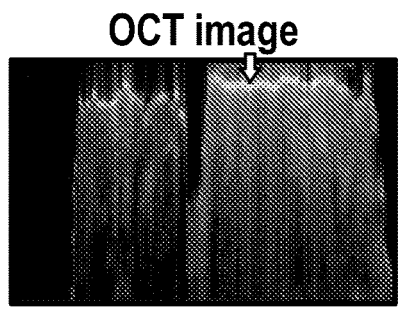
FIG. 9B is an OCT image of the SCC tumor in FIG. 9A using a first scanning trajectory (12 o'clock direction) in FIG. 4A.
Figure 9E:
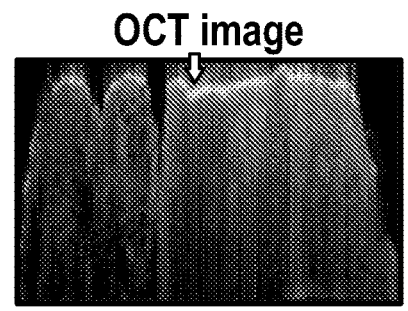
FIG. 9E is an OCT image of the SCC tumor in FIG. 9A using a second scanning trajectory (3 o'clock direction) in FIG. 4A.
Figure 9C:
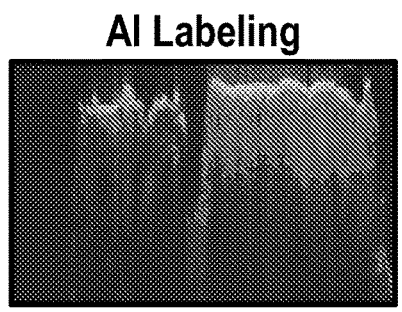
FIG. 9C is a U-Net segmentation image of the OCT image in FIG. 9B.
Figure 9F:
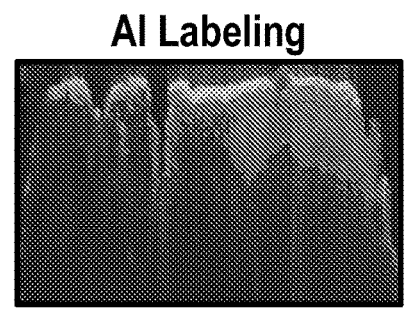
FIG. 9F is a U-Net segmentation image of the OCT image in FIG. 9E.
Figure 9D:
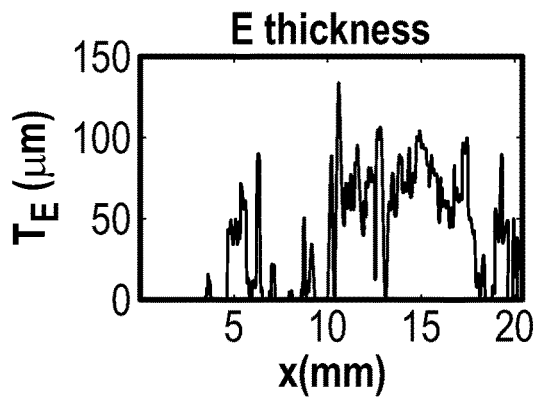
FIG. 9D illustrates an epidermal thickness along the lateral dimension of the OCT image in FIG. 9B.
Figure 9G:
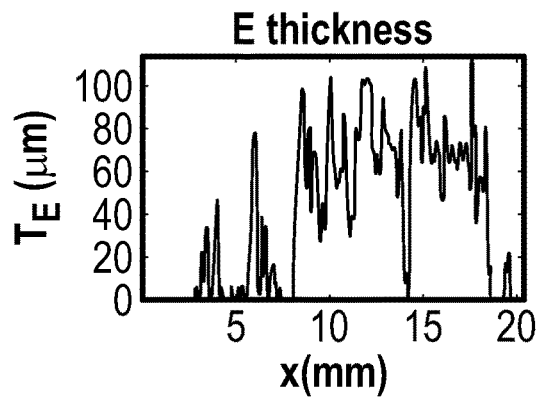
FIG. 9G illustrates an epidermal thickness along the lateral dimension of the OCT image in FIG. 9E.
Figure 9H:
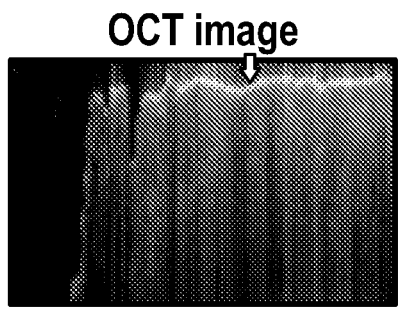
FIG. 9H is an OCT image of the SCC tumor in FIG. 9A using a third scanning trajectory (6 o'clock direction) in FIG. 4A.
Figure 9K:
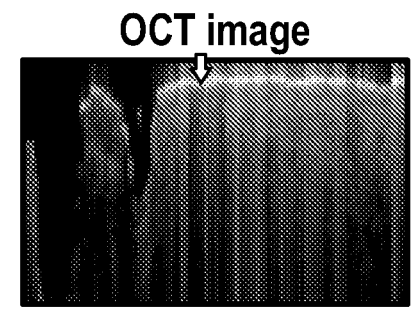
FIG. 9K is an OCT image of the SCC tumor in FIG. 9A using a fourth scanning trajectory (9 o'clock direction) in FIG. 4A.
Figure 9I:
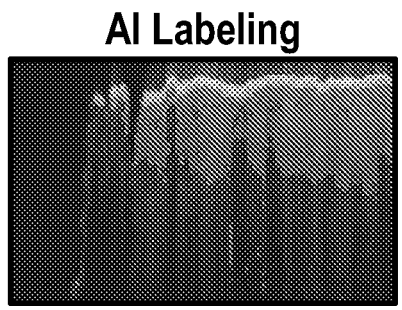
FIG. 9I is a U-Net segmentation image of the OCT image in FIG. 9H.
Figure 9L:
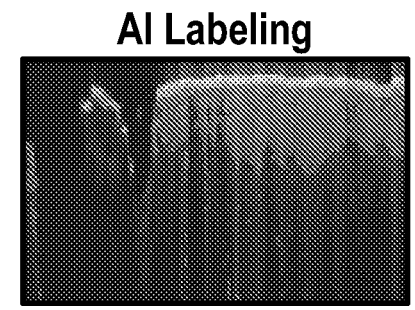
FIG. 9L is a U-Net segmentation image of the OCT image in FIG. 9K.
Figure 9J:
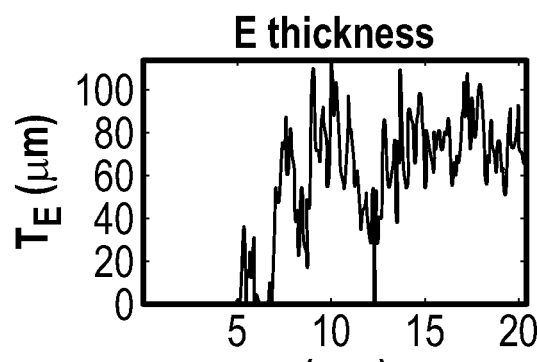
FIG. 9J illustrates an epidermal thickness along the lateral dimension of the OCT image in FIG. 9H.
Figure 9M:
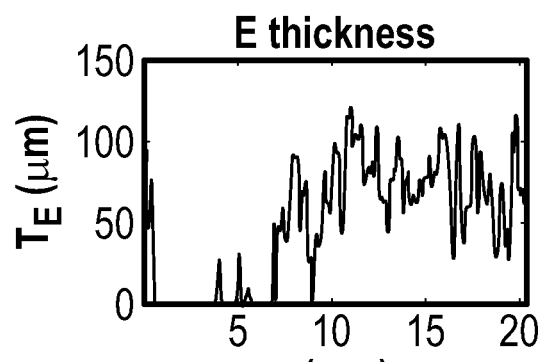
FIG. 9M illustrates an epidermal thickness along the lateral dimension of the OCT image in FIG. 9K.

FIG. 9A is a photograph of a SCC tumor 900 at a forehead of a patient. FIG. 9B is an OCT image of the SCC tumor 900 in FIG. 9A using a first scanning trajectory (12 o'clock direction) in FIG. 4A. FIG. 9C is a U-Net segmentation image of the OCT image in FIG. 9B. FIG. 9D illustrates an epidermal thickness along the lateral dimension of the OCT image in FIG. 9B. FIG. 9E is an OCT image of the SCC tumor 900 in FIG. 9A using a second scanning trajectory (3 o'clock direction) in FIG. 4A. FIG. 9F is a U-Net segmentation image of the OCT image in FIG. 9E. FIG. 9G illustrates an epidermal thickness along the lateral dimension of the OCT image in FIG. 9E. FIG. 9H is an OCT image of the SCC tumor 900 in FIG. 9A using a third scanning trajectory (6 o'clock direction) in FIG. 4A. FIG. 9I is a U-Net segmentation image of the OCT image in FIG. 9H. FIG. 9J illustrates an epidermal thickness along the lateral dimension of the OCT image in FIG. 9H. FIG. 9K is an OCT image of the SCC tumor 900 in FIG. 9A using a fourth scanning trajectory (9 o'clock direction) in FIG. 4A. FIG. 9L is a U-Net segmentation image of the OCT image in FIG. 9K. FIG. 9M illustrates an epidermal thickness along the lateral dimension of the OCT image in FIG. 9K.

Results shown in FIGS. 9B-9M were obtained from the patient with the SCC tumor 900 at his forehead. Prior to imaging, the Mohs surgeon used a metallic marking pen to draw the surgical margin along which the first stage would be excised.

In FIG. 9B, the OCT image was obtained through a manual scanning along the 12 o'clock scanning trajectory via the system 100. The arrow indicates a mark 902 of a metallic ink pen. The right side of the OCT image corresponds normal skin 904. In comparison, the tumor on the left side of the OCT image shows a thin and bright surface layer. Underneath the layer, the OCT signal decays at a faster rate, compared to the decay in the normal skin 904. This is consistent with the clinical photograph in FIG. 9A that shows a tumor with a translucent appearance because of reduced scattering.

In FIG. 9C, for the normal skin 904, ordinary skin architecture is detected (the right side of the labeled image). For the skin tumor 900, the U-Net neural network of the system 100 classifies most pixels underneath the surface layer as "background" pixels, because of the low signal magnitude and lack of structural features.

In FIG. 9D, the thickness of epidermis determined through the U-Net segmentation is small and varies significantly along the lateral dimension. Results obtained from other scanning trajectories in FIGS. 9E-9M show similar contrast between the normal skin 904 and the SCC tumor 900.

Figure 10:
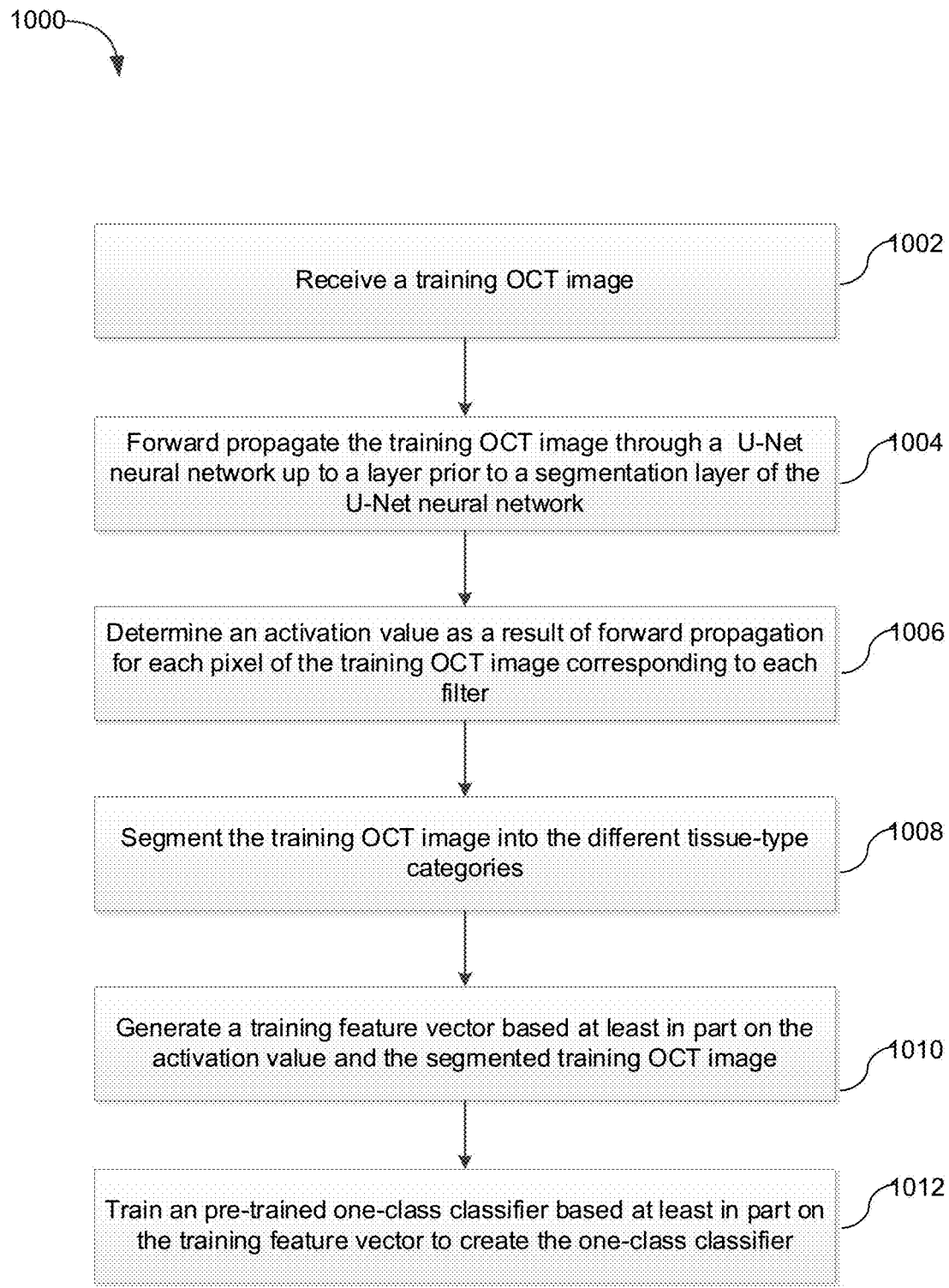
FIG. 10 is an example flowchart illustrating steps 1000 for training a pre-trained one-class classifier to differentiate abnormal tissue from normal skin tissue in accordance with embodiments of the present disclosure.

FIG. 10 is an example flowchart illustrating steps 1000 for training a pre-trained one-class classifier to differentiate abnormal tissue from normal skin tissue in accordance with embodiments of the present disclosure.

In step 1002, the system 100 (e.g., the training engine 150) receives a training OCT image. Dataset for training and validation can have many OCT images obtained from normal skin. However, it is much challenging to acquire images from abnormal or diseased skin, simply because of the limited number of patients. Moreover, different pathology appears different under OCT examination. Hence, it is challenging to establish a balanced dataset to train a classifier that classifies normal skin tissue, and tissues with a variety of pathologies. To overcome this challenge, the one-class classifier of the present disclosure is trained using features extracted only from normal skin tissue. Training OCT images can be a collection of OCT images, each OCT image having normal tissue. The one-class classifier learns the characteristics of normal tissue, and identifies abnormal tissue when different characteristics from normal tissue are observed.

In step 1004, the system 100 forwards propagate the training OCT image through the neural network up to a layer prior to layers for segmentation. For example, features learned by the U-Net architecture 600 can be used to train the pre-trained one-class classifier. The training OCT image can be forward propagated through the trained U-Net network up to a layer right before a segmentation layer. The U-Net architecture 600 can extract features from the training OCT image at different scales and different abstraction layers. An example is described with respect to FIG. 12A.

In step 1006, the system 100 determines an activation value as a result of forward propagation for each pixel of the training OCT image corresponding to each filter. An example is described with respect to FIG. 11.

In step 1008, the system 100 segments the training OCT image into the different tissue-type categories. For example, as shown in FIGS. 6 and 7C, the U-Net architecture 600 can further process the features extracted at different scales and different abstraction layers by performing pixel classification at the segmentation layer. The system 100 can classify each pixel into a specific tissue-type category. For example, the U-Net architecture 600 can classify OCT pixels into categories including air, stratum corneum, epidermis, dermis, and background. Using the results of U-Net segmentation, spatially resolved features can be extracted for a specific transverse location, including the thickness of epidermis ($v_1$) and the spatial variation of epidermal thickness ($v_2$). A multidimensional feature ($v=[v_1, v_2, v_3, \ldots]$) can be extracted from the training OCT image.

In step 1010, the system 100 generates a training feature vector based at least in part on the activation value and the segmented training OCT image. For example, the system 100 can average activation values for each filter ($x_i$ for the ith filter) and use results obtained from all the filters to establish a vector x ($x=[x_1, x_2, \ldots, x_N]'$ and N=16). The system 100 can feed the vector x ($x=[x_1, x_2, \ldots, x_N]'$ and N=16) and/or the feature ($v=[v_1, v_2, v_3, \ldots]$) obtained from the segmented training OCT image into the feature extractor 130 to create the training feature vector for training the pre-trained one-class classifier. An example is described with respect to FIG. 12A.

In step 1012, the system 100 trains the pre-trained one-class classifier based at least in part on the training feature vector to create a trained one-class classifier. The trained one-classifier can separate data in the transformed high-dimensional predictor space to detect outliers, and is effective at producing decision surfaces from high-dimensional feature vectors. The one-class classifier utilizes the facts that OCT images of normal skin are similar and OCT images of skin under pathological conditions are different from those of normal skin to circumvent the need to acquire images from patients with different skin cancers and to train the classifier using OCT images of normal skin obtained from healthy subjects. An example is described with respect to FIG. 12A.

Figure 11:
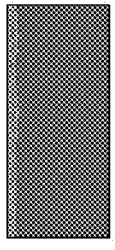
FIG. 11 illustrates an activation value at each pixel corresponding to each filter in accordance with embodiments of the present disclosure.
Figure 11:
Figure 11:
Figure 11:
Figure 11:
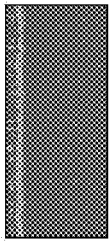
Figure 11:
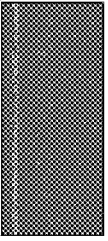
Figure 11:
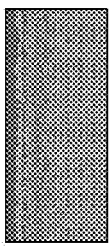
Figure 11:
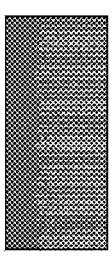
Figure 11:
Figure 11:
Figure 11:
Figure 11:
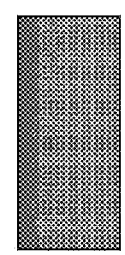
Figure 11:
Figure 11:
Figure 11:
Figure 11:

FIG. 11 illustrates an activation value at each pixel corresponding to each filter in accordance with embodiments of the present disclosure. As shown in FIG. 11, an activation value is created as the result of forward propagation for each pixel corresponding to each filter (N=16 for 16 filters). For each image patch (32 Ascans), the system 100 can average the activation values for each filter ($x_i$ for the $i^{th}$ filter) and use results obtained from all the filters to establish the feature vector x (x=[$x_1$, $x_2$, ..., $x_N$]' and N=16).

Figure 12A:
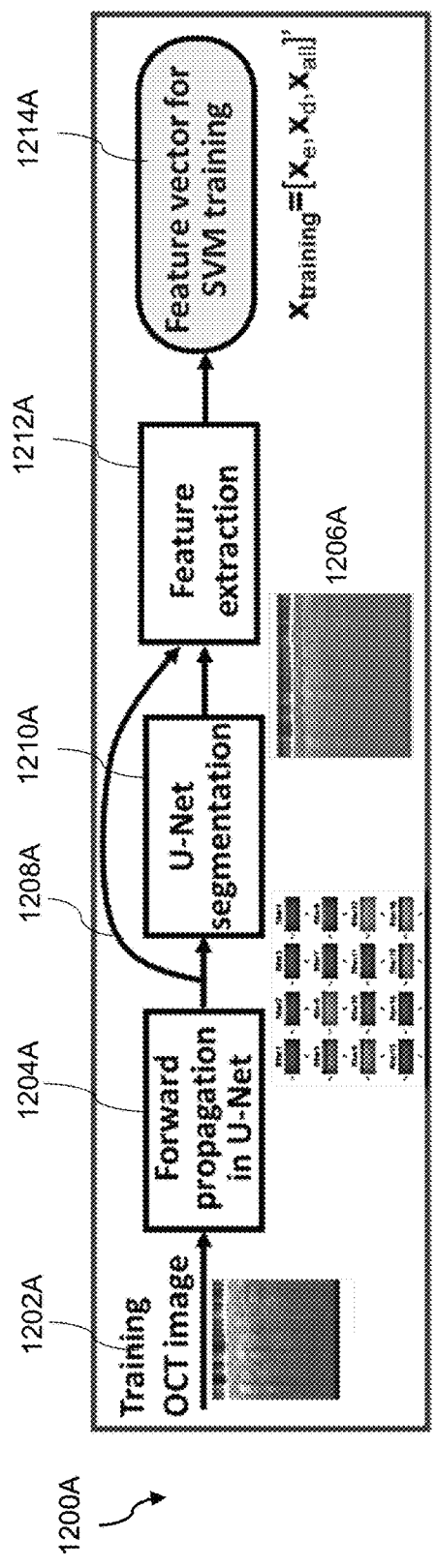
FIG. 12A is an example data flow for training a one-class classifier in accordance with embodiments of the present disclosure.
Figure 12B:
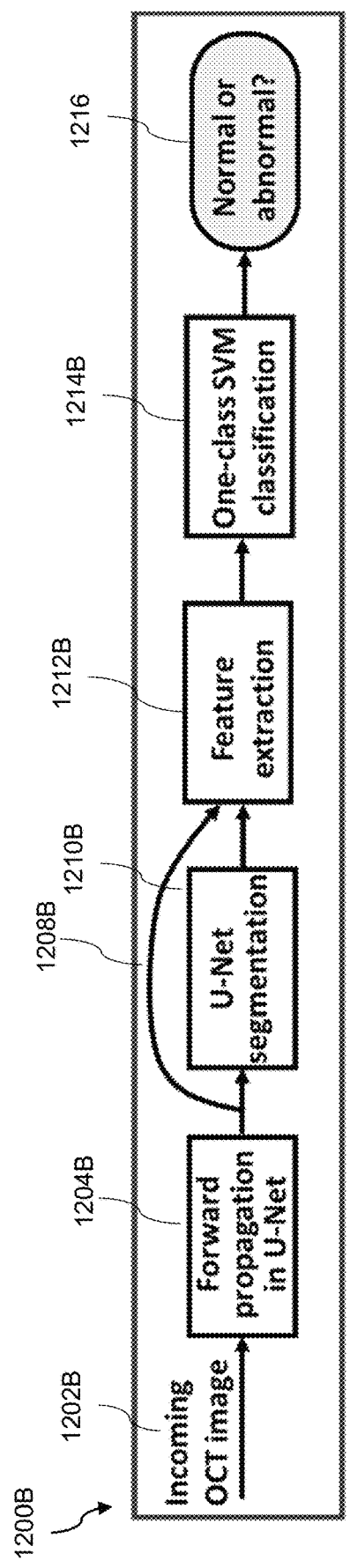
FIG. 12B is an example data flow for applying the trained one-class classifier from FIG. 12A to an incoming OCT image.

FIG. 12A is an example data flow 1200A for training a one-class classifier in accordance with embodiments of the present disclosure. FIG. 12B is an example data flow 1200B for applying the trained one-class classifier from FIG. 12A to an incoming OCT image.

As shown in FIG. 12A, an training image 1202A is input into forward propagation layers in U-Net 1204A. An output 1208A (e.g., the results shown in FIG. 11) from the forward propagation layers in U-Net 1204A is input into a U-Net segmentation layer 1210A and a feature extraction 1212A. An output 1206A (e.g., the results shown in FIG. 7C) from the U-Net segmentation layer 1210A is input into the feature extraction 1212A. The feature extraction 1212A generates feature vectors for training a SVM classifier. With the SVM classifier trained, an incoming OCT image 1202B is activated by a forward propagation layers in U-Net 1204B and segmented by a U-Net segmentation layer 1210B to create a feature vector by a feature extraction 1212B. The feature vector is input into the trained SVM classifier to classify tissue in the incoming OCT image 1202B as normal or abnormal 1216. One-class SVM classifier is used in FIGS. 12A and 12B. It should be understood that a different one-class classifier can be used.

Figure 13:
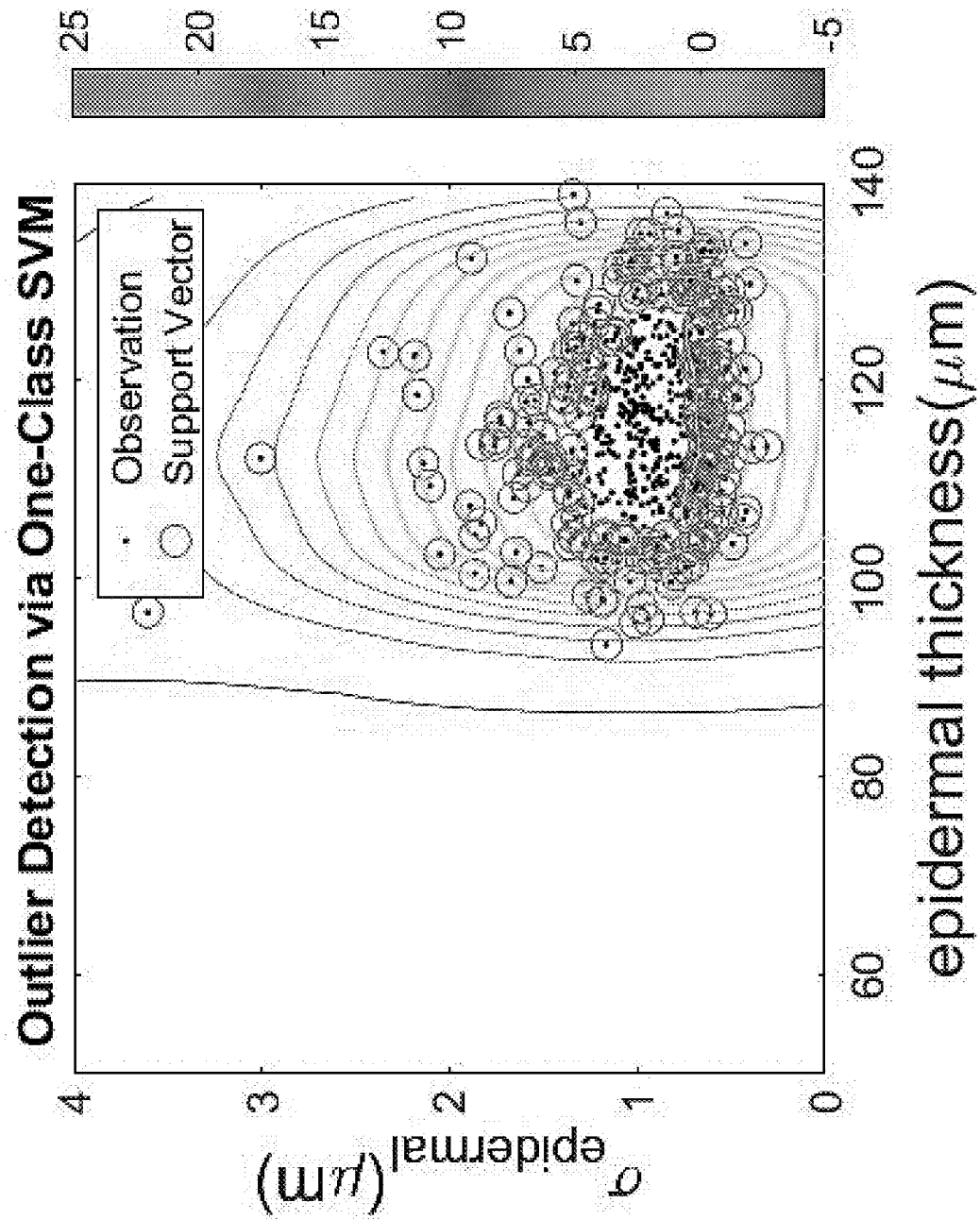
FIG. 13 is a graphical depiction showing an identification of support vectors to detect outlier and skin abnormity using a combination of epidermal thickness and the standard variation of epidermal thickness.

FIG. 13 is a graphical depiction showing an identification of support vectors to detect outlier and skin abnormity using a combination of epidermal thickness and the standard variation of epidermal thickness. As shown in FIG. 13, the support vectors obtained using the combination of epidermal thickness and the standard variation of epidermal thickness (e.g., the vector v described with respect to FIG. 10) are consistent with the observation points, which indicates that the support vectors can represent an outlier of abnormal tissue.

Example Experimental Results

To train the U-Net and the one-class SVM classifier, the OCT imaging platform described in FIGS. 1 and 2A-2D were used to obtain images from 6 healthy subjects. From each subject, the right forearm, left forearm, forehead, neck and palm were scanned. The age of the subjects ranged from 24 to 59. The skin type of the subjects ranged from type II to type IV. Both male and female subjects were measured. Images that had low quality were excluded and a training data set with 32 images was established. Each image had a dimension of 2048 (Ascan number) by 256 (pixel number in each Ascan). Pixels of the images were manually labeled to be air (signal free region), stratum corneum, epidermis, and dermis. The images along with the ground truth (results of manual labeling) were divided into smaller patches (32 Ascan per patch), resulting in 2048 image patches.

Figure 14A:
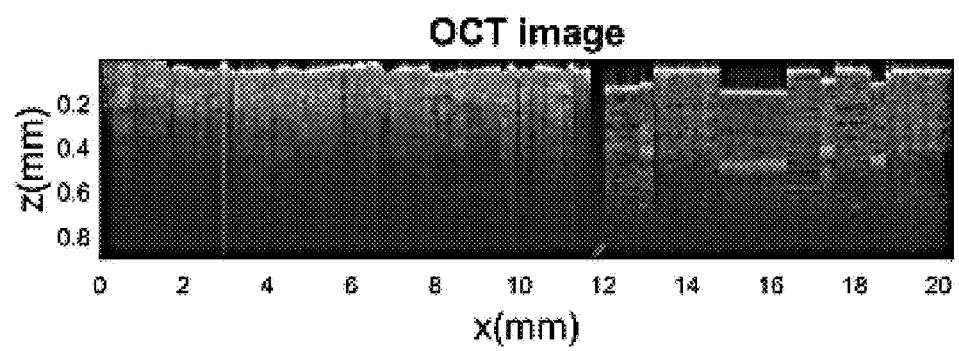
FIG. 14A is an OCT image obtained by scanning a fiber-optic probe across a junction between skin and a nail plate from a healthy subject.
Figure 14B:
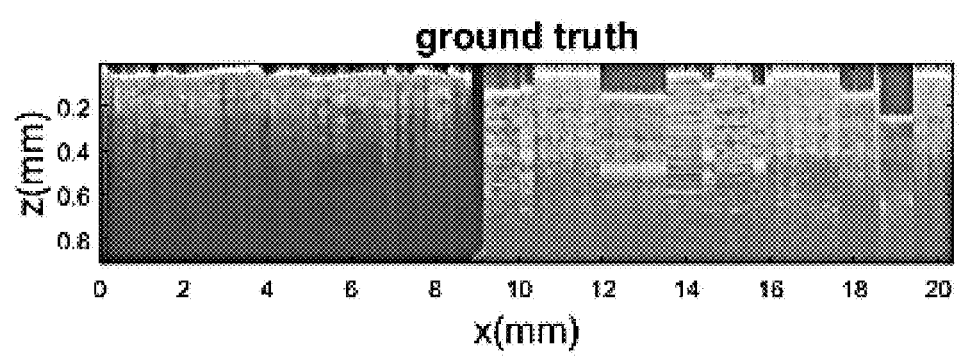
FIG. 14B is a ground truth labeling of normal skin and nail plate (considered as abnormal skin).
Figure 14C:
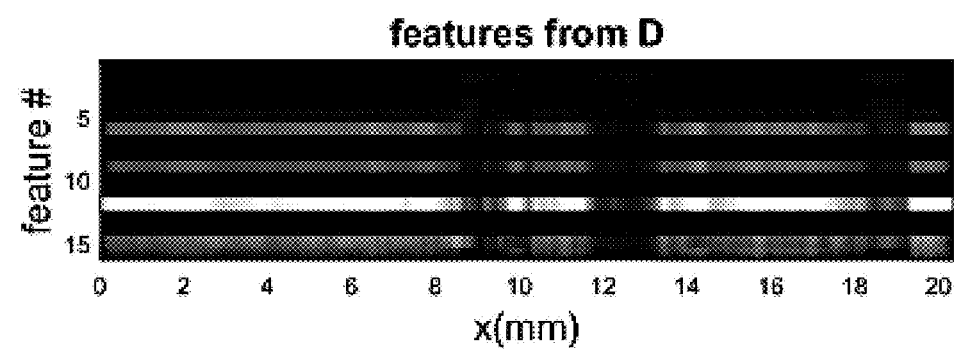
FIG. 14C is an image showing features extracted from dermis pixels at different spatial locations.
Figure 14D:
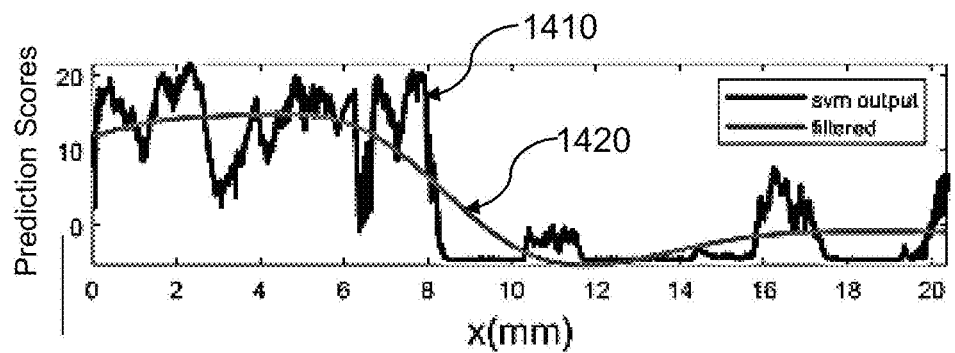
FIG. 14D illustrates a plot of prediction score outputs from the trained SVM before and after low-pass filtering.
Figure 14E:
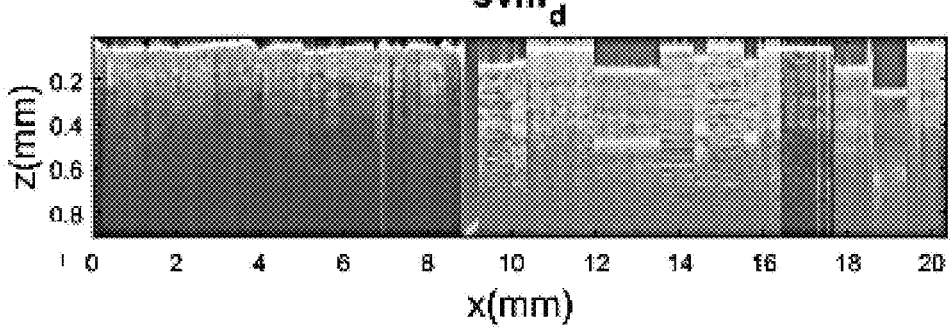
FIG. 14E is an image of abnormal skin identified by a one-class classifier without filtering the prediction scores.
Figure 14F:
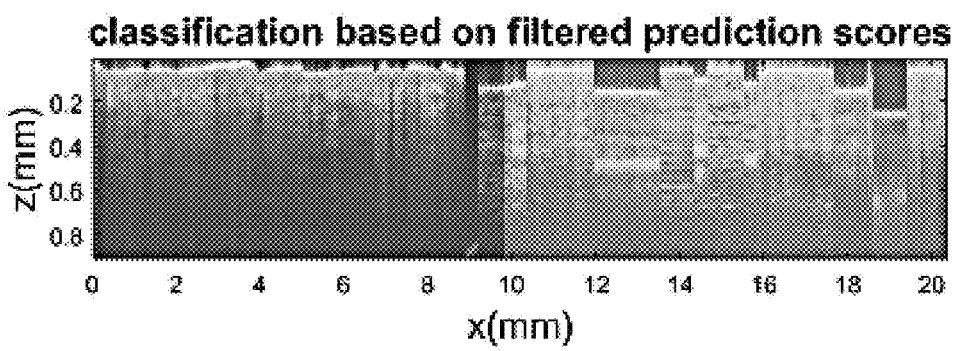
FIG. 14F is an image abnormal skin identified by the one-class classifier after filtering the prediction scores.

FIG. 14A is an OCT image obtained by scanning a fiber-optic probe across a junction between skin and a nail plate from a healthy subject. FIG. 14B is a ground truth labeling of normal skin and nail plate (considered as abnormal skin). FIG. 14C is an image showing features extracted from dermis pixels at different spatial locations. FIG. 14D illustrates a plot of prediction score outputs from the trained SVM before and after low-pass filtering. FIG. 14E is an image of abnormal skin identified by a one-class classifier without filtering the prediction scores. FIG. 14F is an image abnormal skin identified by the one-class classifier after filtering the prediction scores.

To validate that the one-class classifier allowed spatially resolved tissue classification, the fiber-optic OCT probe was scanned at the thumb of a healthy subject, across the junction between the skin and the nail plate. The image obtained is shown in FIG. 14A. The left side of the image corresponds to the skin and the right side of the image corresponds to the nail plate, as shown in FIG. 14B. The signal obtained from the nail was different from OCT signal of the skin and was considered as abnormal. FIG. 14C shows the feature vectors at different lateral locations. These feature vectors ($x_d$) were obtained from pixels labeled as dermis by the U-Net. Using these feature vectors and the classifier trained by normal skin images, the system 100 was able to determine the tissue type at different spatial locations (in FIG. 14D). The prediction scores 1410 can be spatially smoothed (e.g., $5^{th}$ order Butterworth filter, 0.005 cut-off frequency), resulting in the filtered curve 1420 in FIG. 14D. The abnormal skin identified by the classifier are labeled in FIGS. 14E and 14F, using the prediction scores before (unfiltered prediction scores 1410) and after filtering (filtered prediction scores 1420). Result in FIG. 14F suggests that one-class SVM using features extracted from dermis allowed tissue classification (normal and abnormal skin tissue) with spatial resolution.

As described previously, the features are obtained by forward propagating the input image through the network and averaging the activations at the layer before segmentation. To obtain an effective feature vector, pixels that are overwhelmed by noise and labeled as "air" by the U-Nets have to be eliminated for feature extraction. Furthermore, features are extracted by averaging the activations among a specific type of pixel, because different pixel types correspond to different activation values and averaging cross different pixel types will lead to suboptimal classification.

To validate our feature selection strategy, 50% of the images in the data set for normal skin for feature extraction and one-class classification training were used. Vectors were obtained, including $x_{all}$ by averaging activation values for all the pixels without discriminating the pixel type, $x_e$ by averaging activation values for epidermis pixels, and $x_d$ by averaging activation values for dermis pixels. Stratum corneum pixels were not considered, because very few pixels were classified as stratum corneum. The SVM was trained using $x_{all}$, $x_e$, $x_d$, and $x_{e\&d}=[x_e; x_d]$, using a Gaussian kernel function and an outlier-fraction of 10%, and obtained four different classifiers, $SVM_{all}$, $SVM_e$, $SVM_d$, and $SVM_{e\&d}$.

To validate the effectiveness of these classifiers, a validation data set that included the remaining (50%) images in the data set of normal skin and computer synthesized abnormal images were created. Based on the fact that BCCs create upper dermis signal-free cavities with reduced OCT signal magnitude, abnormal images by reducing the signal amplitude to 75% of its original value from a random depth within the dermis were created. For each image within the validation data set, a label (normal or abnormal) was obtained, and feature vectors $x_{all}$, $x_e$, $x_d$, and $x_{e\&d}=[x_e; x_d]$ were calculated. The method described herein were able to predict the tissue type using classifiers obtained from the training process and evaluate the accuracy of classification.

Figure 15:
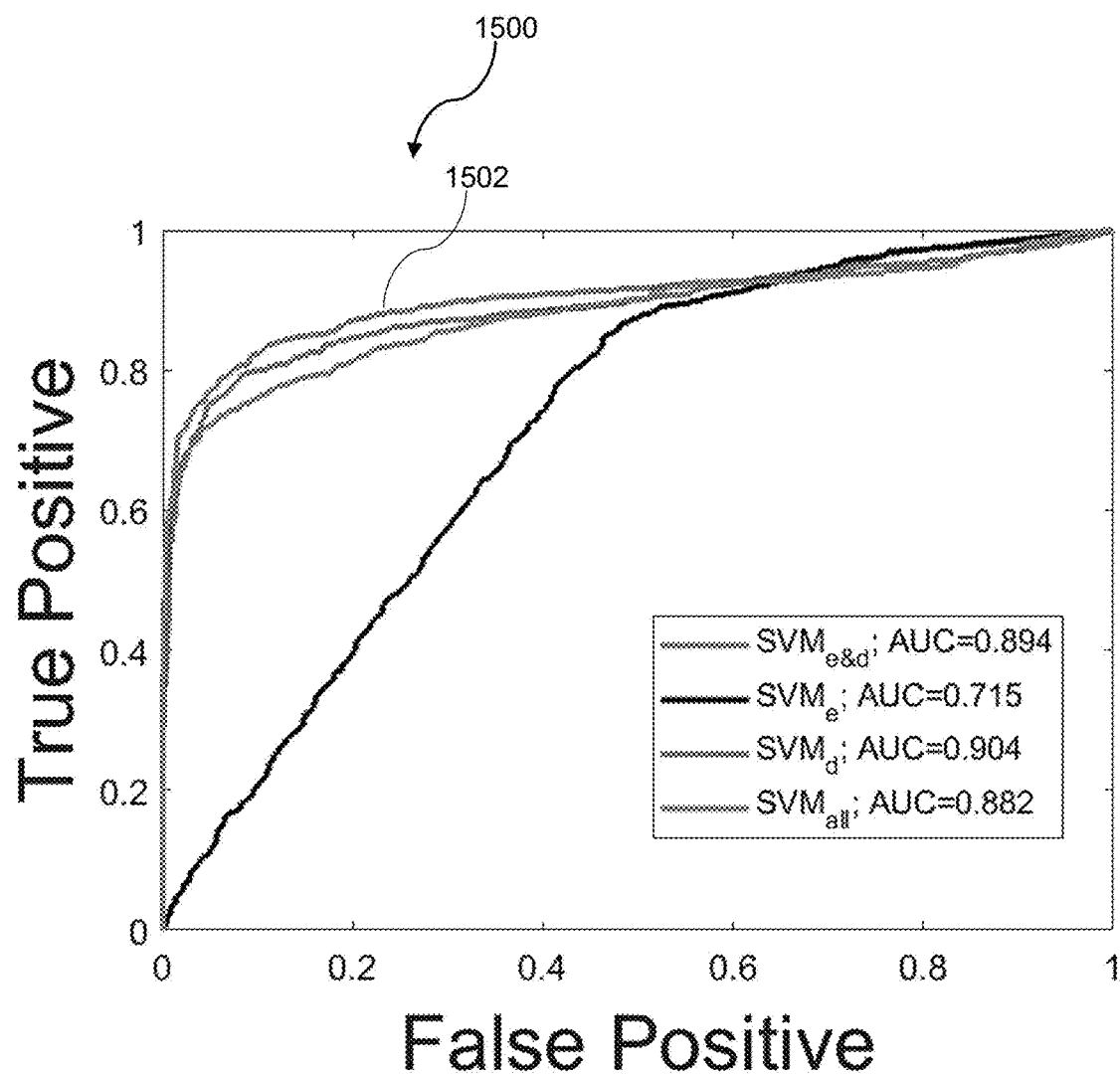
FIG. 15 illustrates receiver operating characteristic (ROC) curves for different classifiers obtained using a validating data set with normal skin images and computer synthesized abnormal images.

FIG. 15 illustrates receiver operating characteristic (ROC) curves 1500 for different classifiers obtained using a validating data set with normal skin images and computer synthesized abnormal images. $SVM_d$ 1502 has the largest area under curve (AUC) value compared with other tissue types. Table 1 shows assessment of classification accuracy when the classifiers were trained with an outlier ratio of 10%.

TABLE 1

|  | Sensitivity | Specificity | Accuracy |
|---|---|---|---|
| $SVM_{e\&d}$ | 0.78 | 0.85 | 0.81 |
| $SVM_e$ | 0.52 | 0.85 | 0.69 |
| $SVM_d$ | 0.87 | 0.85 | 0.86 |
| $SVM_{all}$ | 0.62 | 0.88 | 0.75 |

In a pilot imaging experiments, a patient with basal cell carcinoma (BCC) (superficial and nodular type) was imaged. The patient was a 73-year-old male and the tumor was located at his left cheek. The surgeon labeled the tumor with a marker. Three sets of scans were performed.

Figures 16A, 16B:
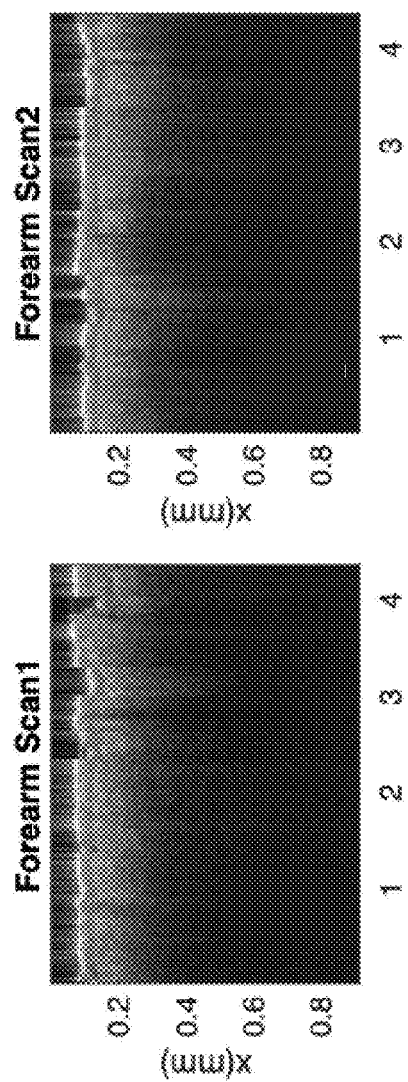
FIGS. 16A and 16B are OCT images of normal tissue from a patient having a basal cell carcinoma tumor.

FIGS. 16A and 16B are OCT images of normal tissue from a patient having a basal cell carcinoma tumor. The normal skin at forearm of the patient was scanned and images were obtained. Similar to other images obtained from normal skin, FIGS. 16A and 16B have clearly visible dermis-epidermis junction (DEJ). The first layer of the skin (stratum corneum) is thin and bright, followed by epidermis with reduced brightness. Underneath is dermis where the signal decreases as depth. To perform automatic tissue assessment, the image obtained from normal forearm skin (256 Ascans) was divided into eight non-overlapping patches (32 Ascans). Following procedures illustrated in FIG. 12B to process each image patch, the U-Net was used to segment the image into different skin layers, extracted feature vectors and used the trained classifier to determine whether the tissue was normal or abnormal. For an input feature vector, the classifier output a prediction value. A positive prediction value corresponded to normal skin tissue, while a negative prediction value corresponded to abnormal. The average prediction values calculated using all the image patches are 1.06 and 0.54, respectively. These values implied that the skin scanned was normal. This was consistent with the fact that we obtained FIGS. 16A and 16B from normal skin.

Figure 16C:
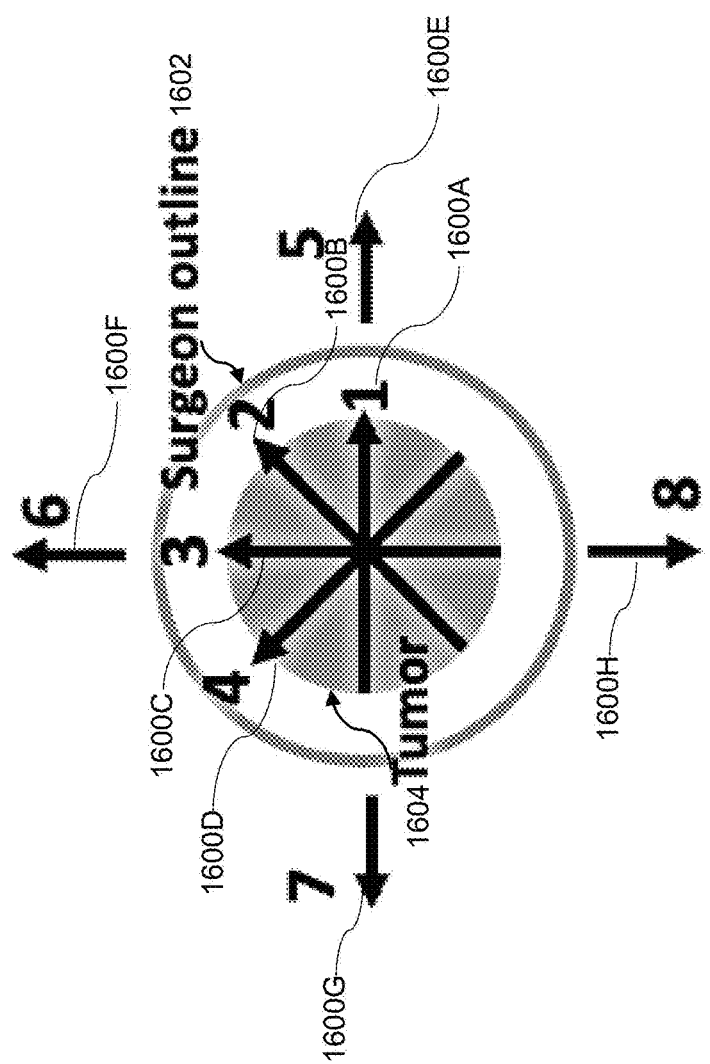
FIG. 16C schematically illustrates scanning trajectories for scanning a tumor of the same patient in FIG. 16A.
Figures 16D, 16E, 16F, 16G:
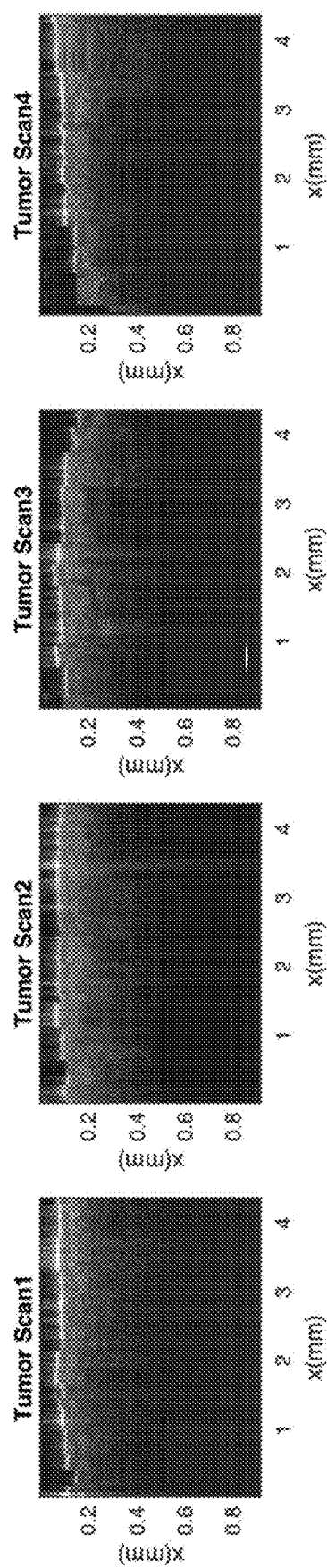
FIG. 16D is an OCT image by scanning a tumor of the same patient in FIG. 16A along a first scanning trajectory in FIG. 16C.
FIG. 16E is an OCT image by scanning the tumor along a second scanning trajectory in FIG. 16C.
FIG. 16F is an OCT image by scanning the tumor in FIG. 16A along a third scanning trajectory in FIG. 16C.
FIG. 16G is an OCT image by scanning the tumor along a fourth scanning trajectory in FIG. 16C.

FIG. 16C schematically illustrates scanning trajectories 1600A-1600H for scanning a tumor 1604 of the same patient in FIG. 16A. FIG. 16D is an OCT image by scanning a tumor of the same patient in FIG. 16A along a first scanning trajectory 1600A in FIG. 16C. FIG. 16E is an OCT image by scanning the tumor along a second scanning trajectory 1600B in FIG. 16C. FIG. 16F is an OCT image by scanning the tumor in FIG. 16A along a third scanning trajectory 1600C in FIG. 16C. FIG. 16G is an OCT image by scanning the tumor along a fourth scanning trajectory 1600D in FIG. 16C.

Compared to the normal skin from the same patient, images obtained from the tumor features disruption of DEJ and reduced OCT signal amplitude starting from upper dermis. To validate the automatic tissue characterization approach described herein, the procedures described in FIG. 12B were followed and negative prediction values for all the images obtained from the tumor were obtained. The average prediction values for all the images were negative, suggesting the region scanned corresponded to abnormal skin tissue.

Figures 16H, 16I, 16J, 16K:
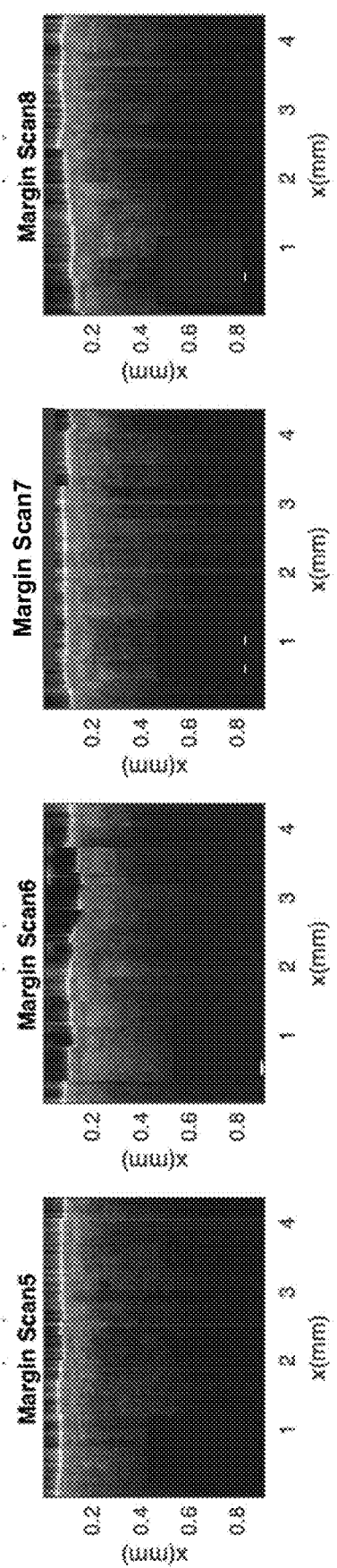
FIG. 16H is an OCT image by scanning a tissue region along a fifth scanning trajectory in FIG. 16C.
FIG. 16I is an OCT image by scanning the tissue region along a sixth scanning trajectory in FIG. 16C.
FIG. 16J is an OCT image by scanning the tissue region along a seventh scanning trajectory in FIG. 16C.
FIG. 16K is an OCT image by scanning tissue region along an eighth scanning trajectory in FIG. 16C.
Figure 17:
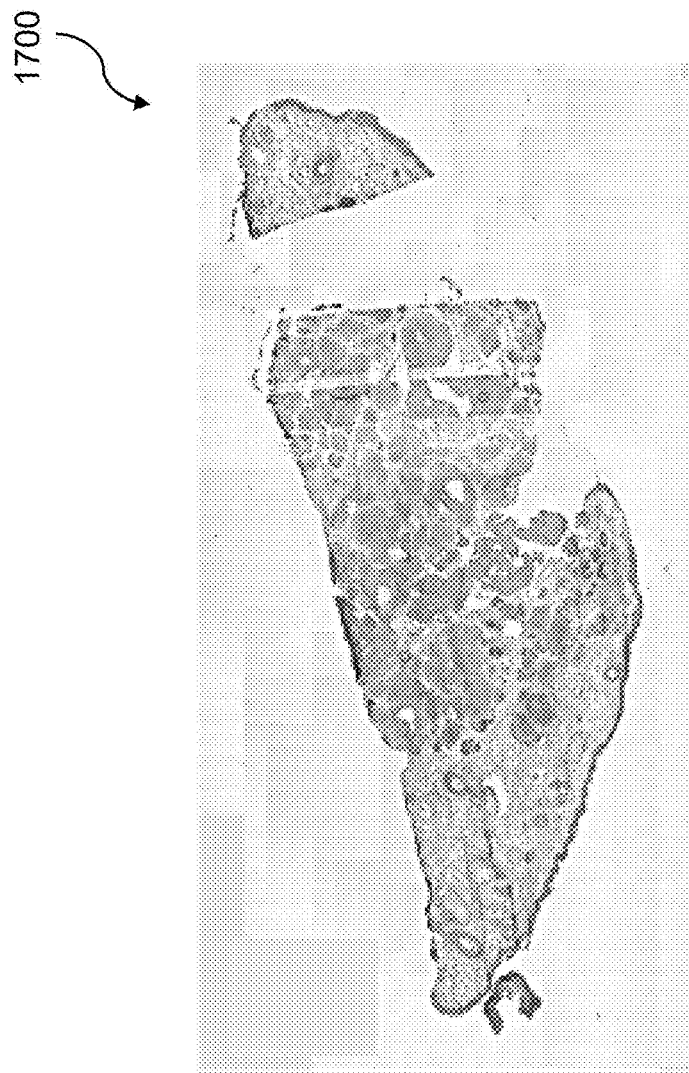
FIG. 17 is an histologic image of scanning areas in FIGS. 16D-16K.

FIG. 16H is an OCT image by scanning a tissue region along the scanning a fifth trajectory 1600E in FIG. 16C. FIG. 16I is an OCT image by scanning the tissue region along a sixth scanning trajectory 1600F in FIG. 16C. FIG. 16J is an OCT image by scanning the tissue region along a seventh scanning trajectory 1600G in FIG. 16C. FIG. 16K is an OCT image by scanning tissue region along an eighth scanning trajectory 1600H in FIG. 16C. FIG. 17 is an histologic image 1700 of scanning areas in FIGS. 16D-16K. The scanning trajectories 1600E-1600H were across a surgeon outline 1602. The average prediction scores for FIGS. 16H and 16I were negative, while the average prediction scores for FIGS. 16J and 16K were positive. This is confirmed by histology 1700 in FIG. 17. Table 2 shows prediction scores and results for FIGS. 16A-16K.

TABLE 2

|  | SVM score | Normal or abnormal |
|---|---|---|
| Normal skin (forearm Scan1) | 4.2 | Normal |
| Normal skin (forearm Scan2) | 2.1 | Normal |
| Tumor (scan 1) | −5.3 | Abnormal |
| Tumor (scan 2) | −3.2 | Abnormal |
| Tumor (scan 3) | −5.3 | Abnormal |
| Tumor (scan 4) | −5.3 | Abnormal |
| Margin (scan 5) | −2.3 | Abnormal (positive margin) |
| Margin (scan 6) | −4.8 | Abnormal (positive margin) |
| Margin (scan 7) | 2.9 | Normal (negative margin) |
| Margin (scan 8) | 6.5 | Normal (negative margin) |

The scan trajectories described with references to FIGS. 16A-16K are example trajectories and the numbering associated with the trajectory is not meant to impart an order with which the trajectories are performed, but rather to distinguish one trajectory from another. Additional or different trajectories can be used to detect and mark a margin between norm and abnormal skin.

Figure 18:
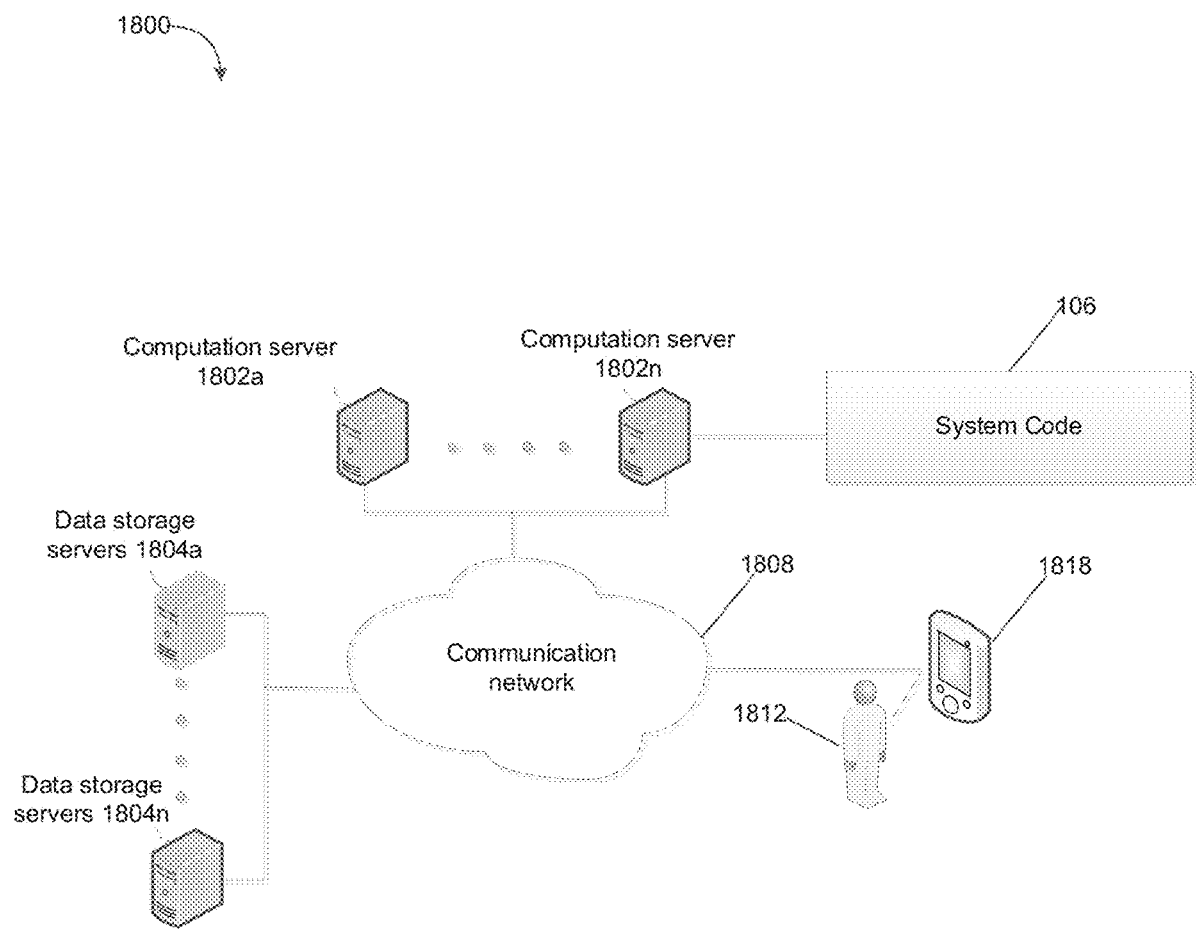
FIG. 18 an example diagram illustrating computer hardware and network components on which the system can be implemented.

FIG. 18 an example diagram illustrating computer hardware and network components on which the system 1800 can be implemented. The system 1800 can include a plurality of computation servers 1802a-1802n having at least one processor (e.g., one or more graphics processing units (GPUs), microprocessors, central processing units (CPUs), tensor processing units (TPUs), application-specific integrated circuits (ASICs), etc.) and memory for executing the computer instructions and methods described above (which can be embodied as system code 106). The system 1800 can also include a plurality of data storage servers 1804a-1804n for storing data. The computation servers 1802a-1802n, the data storage servers 1804a-1804n, and the user device 1810 can communicate over a communication network 1808. Of course, the system 1800 need not be implemented on multiple devices, and indeed, the system 1800 can be implemented on a single (e.g., a personal computer, server, mobile computer, smart phone, etc.) without departing from the spirit or scope of the present disclosure.

Figure 19:
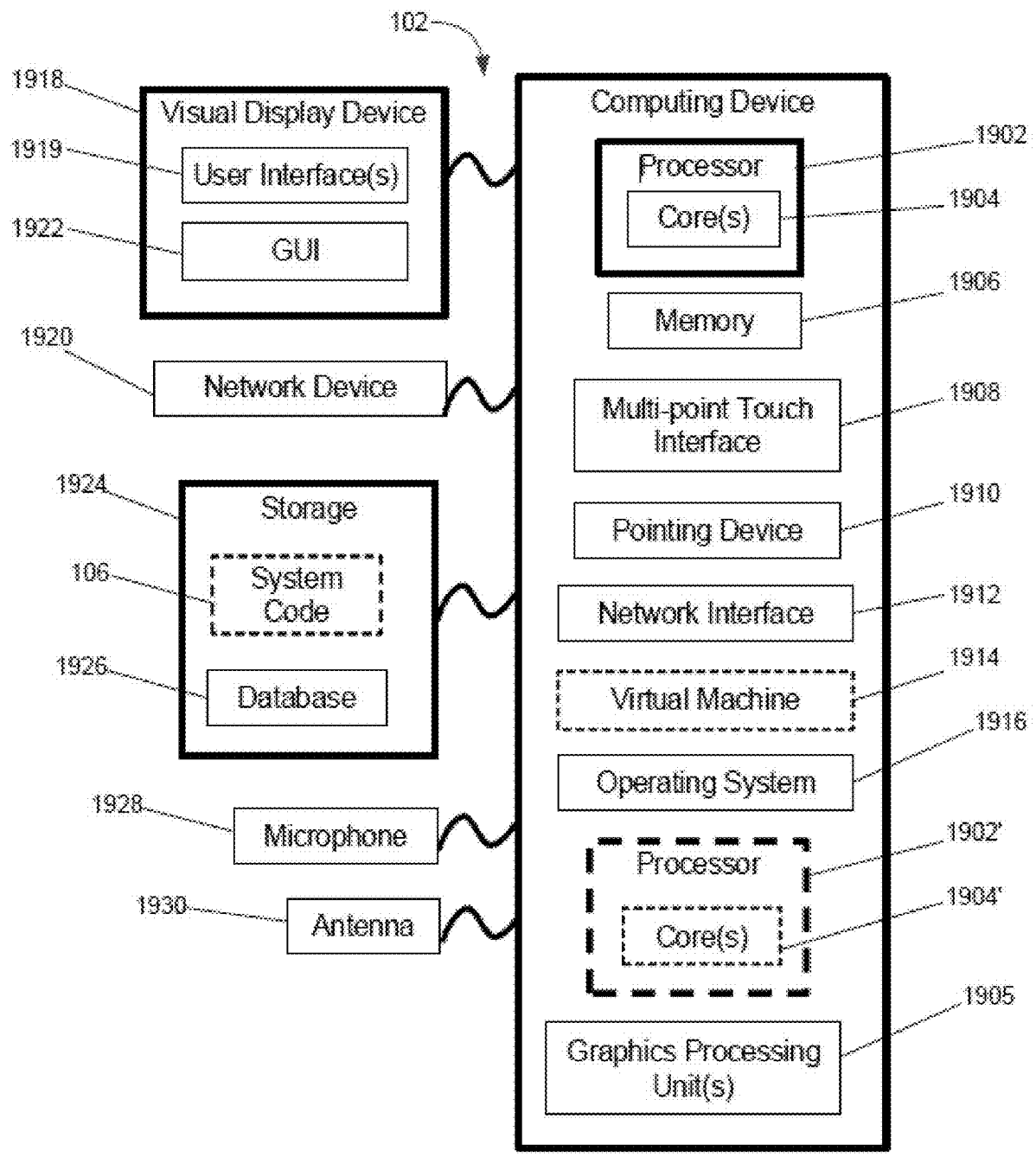
FIG. 19 is an example block diagram of an example computing device that can be used to perform one or more steps of the methods provided by example embodiments.

FIG. 19 is an example block diagram of an example computing device 102 that can be used to perform one or more steps of the methods provided by example embodiments. The computing device 102 includes one or more non-transitory computer-readable media for storing one or more computer-executable instructions or software for implementing example embodiments. The non-transitory computer-readable media can include, but are not limited to, one or more types of hardware memory, non-transitory tangible media (for example, one or more magnetic storage disks, one or more optical disks, one or more USB flash-drives), and the like. For example, memory 1906 included in the computing device 102 can store computer-readable and computer-executable instructions or software for implementing example embodiments. The computing device 102 also includes processor 1902 and associated core 1904, and optionally, one or more additional processor(s) 1902' and associated core(s) 1904' (for example, in the case of computer systems having multiple processors/cores), for executing computer-readable and computer-executable instructions or software stored in the memory 1906 and other programs for controlling system hardware. Processor 1902 and processor(s) 1902' can each be a single core processor or multiple core (1904 and 1904') processor. The computing device 102 also includes a graphics processing unit (GPU) 1905. In some embodiments, the computing system 102 includes multiple GPUs.

Virtualization can be employed in the computing device 102 so that infrastructure and resources in the computing device can be shared dynamically. A virtual machine 1914 can be provided to handle a process running on multiple processors so that the process appears to be using only one computing resource rather than multiple computing resources. Multiple virtual machines can also be used with one processor.

Memory 1906 can include a computer system memory or random access memory, such as DRAM, SRAM, EDO RAM, and the like. Memory 1906 can include other types of memory as well, or combinations thereof. A user can interact with the computing device 102 through a visual display device 1918, such as a touch screen display or computer monitor, which can display one or more user interfaces 1919. The visual display device 1918 can also display other aspects, transducers and/or information or data associated with example embodiments. The computing device 102 can include other I/O devices for receiving input from a user, for example, a keyboard or any suitable multi-point touch interface 1908, a pointing device 1910 (e.g., a pen, stylus, mouse, or trackpad). The keyboard 1908 and the pointing device 1910 can be coupled to the visual display device 1918. The computing device 102 can include other suitable conventional I/O peripherals.

The computing device 102 can also include one or more storage devices 1924, such as a hard-drive, CD-ROM, or other computer readable media, for storing data and computer-readable instructions, applications, and/or software that implements example operations/steps of the system (e.g., the systems 100 and 1000) as described herein, or portions thereof, which can be executed to generate user interface 1919 on display 1918. Example storage device 1924 can also store one or more databases for storing any suitable information required to implement example embodiments. The databases can be updated by a user or automatically at any suitable time to add, delete or update one or more items in the databases. Example storage device 1924 can store one or more databases 1926 for storing provisioned data, and other data/information used to implement example embodiments of the systems and methods described herein.

The system code 106 as taught herein may be embodied as an executable program and stored in the storage 1924 and the memory 1906. The executable program can be executed by the processor to perform the in-situ inspection as taught herein.

The computing device 102 can include a network interface 1912 configured to interface via one or more network devices 1922 with one or more networks, for example, Local Area Network (LAN), Wide Area Network (WAN) or the Internet through a variety of connections including, but not limited to, standard telephone lines, LAN or WAN links (for example, 802.11, T1, T3, 56 kb, X.25), broadband connections (for example, ISDN, Frame Relay, ATM), wireless connections, controller area network (CAN), or some combination of any or all of the above. The network interface 1912 can include a built-in network adapter, network interface card, PCMCIA network card, card bus network adapter, wireless network adapter, USB network adapter, modem or any other device suitable for interfacing the computing device 102 to any type of network capable of communication and performing the operations described herein. Moreover, the computing device 102 can be any computer system, such as a workstation, desktop computer, server, laptop, handheld computer, tablet computer (e.g., the iPad® tablet computer), mobile computing or communication device (e.g., the iPhone® communication device), or other form of computing or telecommunications device that is capable of communication and that has sufficient processor power and memory capacity to perform the operations described herein.

The computing device 102 can run any operating system 1916, such as any of the versions of the Microsoft® Windows® operating systems, the different releases of the Unix and Linux operating systems, any version of the MacOS® for Macintosh computers, any embedded operating system, any real-time operating system, any open source operating system, any proprietary operating system, any operating systems for mobile computing devices, or any other operating system capable of running on the computing device and performing the operations described herein. In some embodiments, the operating system 1916 can be run in native mode or emulated mode. In some embodiments, the operating system 1916 can be run on one or more cloud machine instances.

It should be understood that the operations and processes described above and illustrated in the figures can be carried out or performed in any suitable order as desired in various implementations. Additionally, in certain implementations, at least a portion of the operations can be carried out in parallel. Furthermore, in certain implementations, less than or more than the operations described can be performed.

In describing example embodiments, specific terminology is used for the sake of clarity. For purposes of description, each specific term is intended to at least include all technical and functional equivalents that operate in a similar manner to accomplish a similar purpose. Additionally, in some instances where a particular example embodiment includes multiple system elements, device components or method steps, those elements, components or steps may be replaced with a single element, component or step. Likewise, a single element, component or step may be replaced with multiple elements, components or steps that serve the same purpose. Moreover, while example embodiments have been shown and described with references to particular embodiments thereof, those of ordinary skill in the art will understand that various substitutions and alterations in form and detail may be made therein without departing from the scope of the present disclosure. Further still, other embodiments, functions and advantages are also within the scope of the present disclosure.

While exemplary embodiments have been described herein, it is expressly noted that these embodiments should not be construed as limiting, but rather that additions and modifications to what is expressly described herein also are included within the scope of the invention. Moreover, it is to be understood that the features of the various embodiments described herein are not mutually exclusive and can exist in various combinations and permutations, even if such combinations or permutations are not made express herein, without departing from the spirit and scope of the invention.

What is claimed is:

1. A surgical marker system for delineating a lesion margin in tissue of a subject, the surgical marker system comprising:
    a handheld probe device configured to capture an optical coherence tomography (OCT) image, the OCT image providing an in-depth cross sectional view of a tissue structure beneath a tissue surface, the handheld probe device comprising a handheld probe including:
        a fiber-optic probe assembly configured to direct light to a region of interest and collect light reflected from the region of interest to capture the OCT image; and
        a marker assembly configured to create a visible label on the lesion margin of the subject; and
    a processor coupled to a memory, the processor configured to:
        segment, by a neural network, each pixel of the OCT image into different tissue-type categories;
        generate one or more feature vectors based at least in part on the segmented pixels;
        determine, by a one-class classifier, a boundary location in the OCT image between a normal tissue and an abnormal tissue of the tissue structure based at least in part on the one or more feature vectors; and
        control the marker assembly to create the visible label on a tissue location of the subject, the tissue location corresponding to the boundary location.

2. The surgical marker system of claim 1, wherein the processor is further configured to convert the boundary location from an image-based coordinate system to a subject-based coordinate system.

3. The surgical marker system of claim 1, wherein determining the boundary location between the normal tissue and the abnormal tissue of the tissue structure comprises:
    generating, by the one-class classifier, a prediction score for each pixel of the OCT image, wherein a prediction score indicative of the normal tissue is greater than a threshold value, and a prediction score indicative of the abnormal tissue is less than the threshold value; and
    determining a pixel location as the boundary location, the pixel location corresponding to where a transition occurs between the prediction score indicative of the normal tissue and the prediction score indicative of the abnormal tissue.

4. The surgical marker system of claim 1, wherein the processor is further configured to:
    forward propagate the OCT image through the neural network up to a layer prior to a segmentation layer of the neural network; and
    determine an activation value as a result of forward propagation for each pixel of the OCT image corresponding to each filter,
    wherein generating the one or more feature vectors is further based at least in part on the activation value.

5. The surgical marker system of claim 1, wherein the processor is further configured to:
    determining a spatial variation in thickness of a segmented tissue structure associated with a particular tissue-type category based at least in part on the segmented pixels,
    wherein generating the one or more feature vectors is further based at least in part on the spatial variation in thickness of the segmented tissue structure.

6. The surgical marker system of claim 1, wherein the processor is further configured to:
    receive a training OCT image for training a pre-trained one-class classifier to create the one-class classifier;
    forward propagate the training OCT image through the neural network up to a layer prior to a segmentation layer of the neural network;
    determine an activation value as a result of forward propagation for each pixel of the training OCT image corresponding to each filter;
    segment, using the segmentation layer, the training OCT image into the different tissue-type categories;
    generate a training feature vector based at least in part on the activation value and the segmented training OCT image; and
    train the pre-trained one-class classifier based at least in part on the training feature vector to create the one-class classifier.

7. The surgical marker system of claim 6, wherein the training OCT image corresponds to non-cancerous tissues, and the one-class classifier is trained to recognize the non-cancerous tissues.

8. The surgical marker system of claim 1, wherein each of the one or more OCT images is captured by manually or automatically moving the fiber-optic probe assembly across the region of interest with a first arbitrary lateral field of view.

9. The surgical marker system of claim 1, wherein the marker assembly comprises a marker carrier and a motor, the motor configured to change a position of the marker carrier relative to the subject, wherein controlling the marker assembly to create the visible label on the tissue location of the subject comprises:
    controlling the motor to place, from a rest location of the marker carrier, the marker carrier proximate to the tissue location based at least in part on the determination of the boundary location such that the marker carrier is activated to create the visible label on the tissue location; and
    subsequent to creation of the visible label on the tissue location, controlling the motor to move the marker carrier back to the rest location.

10. The surgical marker system of claim 1, wherein the neural network is a U-Net convolution neural network.

11. The surgical marker system of claim 1, wherein the one-class classifier is a one-class support vector machine (SVM) classifier.

12. The surgical marker system of claim 1, wherein the tissue structure is a skin structure, and the different tissue-type categories comprise a stratum corneum category, an epidermis category, and a dermis category.

13. A method for delineating a lesion margin of a subject, the method comprising:
    capturing an optical coherence tomography (OCT) image, the OCT image providing an in-depth cross sectional view of a tissue structure beneath a tissue surface;
    segmenting, by a neural network, each pixel of the OCT image into different tissue-type categories;
    generating one or more feature vectors based at least in part on the segmented pixels;
    determining, by a one-class classifier, a boundary location in the OCT image between a normal tissue and an abnormal tissue of the tissue structure based at least in part on the one or more feature vectors; and
    controlling a marker assembly to create a visible label on a tissue location of the subject, the tissue location corresponding to the boundary location.

14. The method of claim 13, further comprising:
converting the boundary location from an image-based coordinate system to a subject-based coordinate system.

15. The method of claim 13, wherein determining the boundary location between the normal tissue and the abnormal tissue of the tissue structure comprises:
generating, by the one-class classifier, a prediction score for each pixel of the OCT image, wherein a prediction score indicative of the normal tissue is greater than a threshold value, and a prediction score indicative of the abnormal tissue is less than the threshold value; and
determining a pixel location as the boundary location, the pixel location corresponding to where a transition occurs between the prediction score indicative of the normal tissue and the prediction score indicative of the abnormal tissue.

16. The method of claim 13, further comprising:
forward propagating the OCT image through the neural network up to a layer prior to a segmentation layer of the neural network; and
determining an activation value as a result of forward propagation for each pixel of the OCT image corresponding to each filter,
wherein generating the one or more feature vectors is further based at least in part on the activation value.

17. The method of claim 13, further comprising:
determining a spatial variation in thickness of a segmented tissue structure associated with a particular tissue-type category based at least in part on the segmented pixels,
wherein generating the one or more feature vectors is further based at least in part on the spatial variation in thickness of the segmented tissue structure.

18. The method of claim 13, further comprising:
receiving a training OCT image for training a pre-trained one-class classifier to create the one-class classifier;
forward propagating the training OCT image through the neural network up to a layer prior to a segmentation layer of the neural network;
determining an activation value as a result of forward propagation for each pixel of the training OCT image corresponding to each filter;
segmenting, using the segmentation layer, the training OCT image into the different tissue-type categories;
generating a training feature vector based at least in part on the activation value and the segmented training OCT image; and
training the pre-trained one-class classifier based at least in part on the training feature vector to create the one-class classifier.

19. The method of claim 18, wherein the training OCT image corresponds to non-cancerous tissues, and the one-class classifier is trained to recognize the non-cancerous tissues.

20. The method of claim 13, wherein the marker assembly comprises a marker carrier and a motor, the motor configured to change a position of the marker carrier relative to the subject, wherein controlling the marker assembly to create the visible label on the tissue location comprises:
controlling the motor to place, from a rest location of the marker carrier, the marker carrier proximate to the tissue location based at least in part on the determination of the boundary location such that the marker carrier is activated to create the visible label on the tissue location; and
subsequent to creation of the visible label on the tissue location, controlling the motor to move the marker carrier back to the rest location.

\* \* \* \* \*